(12) United States Patent
Chu et al.

(10) Patent No.: US 6,949,521 B2
(45) Date of Patent: Sep. 27, 2005

(54) THERAPEUTIC AZIDE COMPOUNDS

(75) Inventors: Chung K. Chu, Athens, GA (US); Lakshmi P. Kotra, Detroit, MI (US); Konstantine Manouilov, Omaha, NE (US); Jinfa Du, Irvine, CA (US); Raymond Schinazi, Decatur, GA (US)

(73) Assignees: The University of Georgia Research Foundation, Inc., Athens, GA (US); Emory University, Atlanta, GA (US)

( * ) Notice: Subject to any disclaimer, the term of this patent is extended or adjusted under 35 U.S.C. 154(b) by 396 days.

(21) Appl. No.: 09/849,870

(22) Filed: May 4, 2001

(65) Prior Publication Data

US 2001/0036930 A1 Nov. 1, 2001

Related U.S. Application Data

(62) Division of application No. 09/033,996, filed on Mar. 3, 1998, now Pat. No. 6,271,212, which is a continuation of application No. PCT/US96/14494, filed on Sep. 6, 1996.
(60) Provisional application No. 60/003,383, filed on Sep. 7, 1995.

(51) Int. Cl.$^7$ .......................... A01N 43/04; A61K 31/70
(52) U.S. Cl. ............................ 514/45; 514/25; 514/46; 514/47; 514/49; 514/50; 514/51; 514/117; 514/198; 514/200; 540/336; 540/215; 544/80; 544/264; 536/4.1; 536/23.23; 536/23.76; 536/26.7; 536/27.14; 536/27.4
(58) Field of Search ............................. 514/24, 45, 46, 514/47, 48, 49, 50, 51, 117, 198, 200; 540/215, 336; 544/80, 264; 536/4.1, 23.23, 23.76, 26.7, 27.14, 27.4, 27.61, 27.62

(56) References Cited

U.S. PATENT DOCUMENTS

| | | | |
|---|---|---|---|
| 4,724,232 A | | 2/1988 | Rideout et al. ............... 514/50 |
| 4,818,538 A | | 4/1989 | Rideout et al. ............. 424/436 |
| 4,874,609 A | | 10/1989 | Rideout et al. ............ 424/85.4 |
| 5,180,824 A | * | 1/1993 | Bauman et al. ............. 544/251 |
| 5,457,187 A | * | 10/1995 | Gmeiner et al. ........... 536/25.5 |
| 5,602,246 A | | 2/1997 | Baumann et al. .......... 536/55.3 |
| 5,668,270 A | | 9/1997 | Baumann et al. ........ 536/26.71 |
| 6,271,212 B1 | * | 8/2001 | Chu et al. ..................... 514/45 |

FOREIGN PATENT DOCUMENTS

| | | |
|---|---|---|
| DE | 3 627 024 | 4/1987 |
| EP | 0 145 207 | 6/1985 |
| EP | 0 217 207 | 4/1987 |
| EP | 0 400 686 | 12/1990 |

OTHER PUBLICATIONS

Kotra, L.P. et al. "Synthesis, Biotransformation, and Pharmacokinetic Studies of 9–(β–D–Arabinofuranosyl)–6–azidopurine: A Prodrug for Ara–A Designed To Utilize the Azide Reduction Pathway" *J. Med. Chem.* 39, 5202–5207 (1996).

Adamiak et al., "Synthesis of 6–Substituted Purines and ribonucleosides with N–(6–Purinyl)pyridinium Salts," *Angewandte Chemie, Intl. Ed.*, 24(12):1054–1055 (Dec., 1985).

Agarwal, R.P. et al., "Clinical Pharmacology of 9–β–D–Arabinofuranosyladenine in Combination with 2'–Deoxycoformycin," *Cancer Res.*, 42(9):3884–3886 (Sep., 1982).

Anderson, B.D. et al., "Uptake Kinetics of 2',3'–Dideoxyinosine into Brain and Cerebrospinal Fluid of Rats: Intravenous Infusion Studies," *J. Pharmacol. Exp. Ther.*, (1990) 253(1):113–118.

Andrei, G. et al., "Comparative Activity of Various Compounds Against Clinical Strains of Herpes Simplex Virus," *Eur. J. Clin. Microbiol. Infect. Diseases*, (1992) 11(2):143–151.

Balzarini, J. And DeClercq, E., "The Antiviral Activity of 9–β–D Arabinofuranosyladenine is Enhanced by the 2',3'–Dideoxyriboside, the 2',3'–Didehydro–2',3'–Dideoxyriboside and the 3'–Azido–2',3'–Dideoxyriboside of 2,6–Diaminopurine," *Biochem. Biophys. Res. Commun.*, (1989) 159:61–67.

Barchi, J.J. Jr. et al., "Potential Anti–AIDS bDrugs. Lipophilic, Adenosine Deaminase–Activated Prodrugs," *J. Med. Chem.*, (1991) 34:1647–1655 (Issue No. 5).

Budavari et al. (Eds.), *The Merck Index, 11th Edition*, Merck & Co., Rahway, NJ, Nov. 1989, p. 1597, see entry No. 10023 and references therein.

Cass, C.E. et al., "Antiproliferative Effects of 9–β–D Arabinofuranosyladeniine–5'–Monophosphate and Related Compounds in Combination with Adenosine Deaminase Inhibitors Against Mose Leukemia L1210/C2 Cells in Culture," *Cancer Res.*, 39(5):1563–1569, (May, 1979).

Cass E.C., "9–β–D–Arabinofuranosyladenine (Ara–A)," In *Antibiotics. Mechanism of Action of Anti–Eukaryotic and Antiviral Compounds*; Hahn, F.E., Ed.; Springer–Verlag: New York (1979) V: 85–109.

(Continued)

Primary Examiner—James O. Wilson
Assistant Examiner—Patrick T. Lewis
(74) Attorney, Agent, or Firm—Henry D. Coleman; R. Neil Sudol; William J. Sapone

(57) ABSTRACT

Pharmaceutical prodrug compositions are provided comprising azide derivatives of drugs which are capable of being converted to the drug in vivo. Azide derivatives of drugs having amine, ketone and hydroxy substituents are converted in vivo to the corresponding drugs, increasing the half-life of the drugs. In addition azide prodrugs are often better able to penetrate the blood-brain barrier than the corresponding drugs. Especially useful are azide derivatives of cordycepin, 2'-F-ara-ddI, AraA, acyclovir, penciclovir and related drugs. Useful azide prodrugs are azide derivatives of therapeutic alicyclic amines, ketones, and hydroxy-substituted compounds, including aralkyl, heterocyclic aralkyl, and cyclic aliphatic compounds, where the amine or oxygen moiety is on the ring, or where the amine or oxygen moiety is on an aliphatic side chain, as well as therapeutic purines and pyrimidines, nucleoside analogs and phosphorylated nucleoside analogs.

8 Claims, 7 Drawing Sheets

OTHER PUBLICATIONS

Cass, C.E. and Ah–Yeung, T.H., "Enhancement of 9–β–D–Arabinofuranosyladenine Cytotoxicity to Mouse Leukemia L1210 in vitro by 2'–Deoxycoformycin," *Cancer Res.*, (1976) 36:1486–1491 (Apr., 1976).

Chatis, P.A. and Crumpacker, C.S., "Resistance of Herpesviruses to Antiviral Drugs," *Antimicrob. Agents and Chemother.*, (1992) 36:1589–1595 (Issue No. 8, Aug., 1992).

Chien, R.N. and Liaw, Y.F., "Drug Therapy in Patients with Chronic Type B Hepatitis," *J. Formos. Med. Assoc.*, (1995) 94(suppl. 1):S1–S9 (*English Abstract only*)(Jun., 1995).

Chu, C.K. et al., "Synthesis and Structure–Activity Relationships of 6–Substituted 2',3'–Dideoxypurine Nucleosides as Potential Anti–Human Immunodeficiency Virus Agents," *J. Med. Chem.*, (1990) 33:1553–1561 (Issue No. 6).

Collins, J.M. et al., "Pyrimidiine Dideoxyribonucleosides: Seletivity of Penetration into Cerebrospinal Fluid," *J. Pharmacol, Exp. Ther.*, (1988) 245(2):466–470.

Cretton, E.M. and Sommadossi, J–P., "Reduction of 3'–Azido–2',3'–Dideoxynucleosides to Their 3'–Amino Metabolite is Mediated by Cytochrome P–450 and NADPH–Cytochrome P–450 Reductase in Rat Liver Microsomes," *Drug Metab. Dispos.*, (1993) 21:946–950 (No. 5).

Cretton, E.M. et al., "Catabolism of 3'–Azide–3'–Deoxythymidine in Hepatocytes and Liver Microsomes with Evidence of Formation of 3'–Amino–3'–Deoxythimidine, a Highly Toxic Catabolite for Human Bone Marrow Cells," *Molec. Pharmacol.*, (1991), 39:258–266.

Darby, G. (1995), "In Search of the Perfect Antiviral," *Antiviral Chem. & Chemother.*, 6:54–63.

Denis, J. et. al., "Treatment of Superficial Herpes Simplex Keratitis with Vidarabine (Vira A): Multicenter Study of 100 Cases," *J. Fr. Ophthalmol.*, (1990) 13:143–150 (*English Abstract Only*) (Issue No. 3).

Drach, J.C. and Shipman, C. Jr., "The Selective Inhibition of Viral DNA Synthesis by Chemotherapeutic Agents: an Indicator of Clinical Usefulness?" *Ann. NY Acad Sci.*, (1977) 284:396–409.

Drusano, G.L. et al., "Impact of Bioavailability on Determination of the Maximal Tolerated Dose of 2',3'–Dideoxyinosine in Phase 1 Trails," *Antimicrob. Agents Chemotherapy*, (1992) 36(6):1280–1283 (Jun., 1992).

Faulds, D. and Brogden, R.N., "Didianosine: a Review of Its Antiviral Activity, Pharmacokinetics Properties and Therapeutic Potential in Human Immunodeficiency Virus Infection," *Drugs*, (1992) 44:94–116 (Issue No. 1).

Frederiksen, S. and Klenow, H. (1975), "3–Deoxyadenosine and Other Polynucleotide Chain Terminators," *In Handbook of Experimental Pharmacology*, (A.C. Sartorelli and G. Johnes, Ed.) 657–689. (Chapter 66).

Fu, X.X., "Therapeutic Effect of Combines Treatment with Ara–A, Dauriciine and Chinese Herbs in Chronic Hepatitis B Infection," *Chung. Hua. Nei Ko. Tas. Chih*, (19991) 30(8):498–501 (*English Abstract Only*) (Aug., 1991).

Gerlowski, L.E. and Jain, R.K., "Physiologically Based Pharmacokinetic Modeling: Principles and Applications," *J. Pharm. Sci.*, (1983) 72:1103–1126 (Oct., 1983).

Gibaldi, M. and Perrier, D., "Clearance Concepts." In: *Pharmacokinetics*, 2nd ed., Marcel Dekker Inc., New York (1982) 319–353.

Hakimelahi, G. H. and Khalafi–Nezhad, A. "The Role of Chloromethyl Ethers in the Formation of N(7)– and N(9)—Alkylated Isomers of Adenine Synthesis of 2–[9–(Ethoxymethyl)Adenyl] Phoshonate", *J. Sci., I. R. Iran*, 1(3): pp. 192–196, 1990.

Jansen, R. W. et al., "Coupling of Antiviral Drug Ara–AMP to Lactosaminated Albumin Leads to Specfic Uptake in Rat and Human Hepatocytes," *Hepatology* (1993) 18:146–152 (Jul., 1993).

Johns, D.G. and Adamson, R.H. (1976), "Enhancement of the Biological Activity of Cordycepin (3'–Dexoyadenonsine) by the Adenosine Deaminase Inhibitor 2'–Deoxycoformycin," *Biochem. Pharmacol.* (1976) 25:1441–1444.

Johnson et al., "Synthesis of Potential Anticancer Agents. XIII> Ribosides of 6–Substituted Purines," *J. American Chemical Society*, 80:699–702 (Mar.–Apr. 1994).

Kamali, F., et al. (1988), "Medicinal Azides Part 3. The Metabolism of the Investigational Antitumor Agent Meta–Azidepyrimethamine in Mouse tissue in vitro," *Xenobiotica* 18: 1157–1164.

Kojima et al. "Synthesis and Structure–Activity Relationships of 2',3'–Dideoxypurine Nucleosides as Potential Antiretroviral Agents," Oxford University Press: Abstract, 1991.

Koudriakova, T. et al., "In vitroand in vivo Evaluation of 6–Azido–2', 3'–Dideoxy–2'–Fluoro–β–D–Arabinofuranosylpurine (FAAddP) and 6–Methyl–2', 3'–Dideoxy–2'–Fluoro–β–D–Arabinofuranosyladenine (FMAddA) as Prodrugs of the Anti–HIV Nucleosides, 2'–F–Ara–ddA and 2'–F–Ara–ddI," (1996) *J. Med. Chem.* 39(23):4676–4681.

Kumar, R., et al., "Synthesis, in vitro Biological Stability, and Anti–HIV Activity of 5–Halo–6–Alakoxy (or Azide) – 5,6–Dihydro–3'–Azido–3'Deoxythymidine (AZT)," *J. Med. Chem.* 37:4297–4306 (Issue No. 25).

LePage, G.A. et al., "Enhancement of Antitumor Activity of Arabinofuranosyladene by 2'–Deoxycoformycin," *Cancer Res.*, 36(4):1481–1485 (Apr., 1976).

Marquez, V.E. et al., "Acid–Stable 2'–Fluoro Purine Dideoxynucleosides as Active Agents Against HIV," *J. Med. Chem.* (1990) 33: 978–985 (Issue No. 3).

Miser, J.S. et al., "Lack of Significant Activity of 2'–Deoxycoformycin Alone or in Combination with Adenine Arabinoside in Relapsed Childhood Acute Lymphoblastic Leukemia. A Randomized Phase II Trial from Children's Cancer Study Group," *Am. J. Clin. Oncol.* (1992) 15:490–493 (Issue No. 6).

Montgomery et al, "A Convenient Method for the Synthesis of 2–Fluoro Adenosine," *J. Organic Chemistry*, 33(1):432–434 (Jan., 1968).

Nicholls, D., et al. (1991), "Medicinal Azides. Part 8. The in vitro Metabolism of P–Substituted Phenyl Azides," *Xenobiotica* 21:935–943. (Issue No. 7).

Nitta, K. et al., "Sensitivities to Other antiviral Drugs and Thymidine Kinase Activity of Aciclovir–Resistant Herpes Simplex Virus Type I," *Nippon. Ganka. Gakkai. Zasshi* (1994) 98:513–519 (*English Abstract Only*) (Jun. 1994).

Ozala et al., "On the Synthesis of 8–Heteroaryl–Substituted 9–(β–D–ribufuranosyl)–2, 6–diaminopurines through Pd–Catalyzed Coupling in the Presence of Cupric Oxide," *Journal of Heterocyclic Chemistry*, 32(3):863–866 (May–Jun., 1995).

Placidi, L. et al., "Reduction of 3'–Azido–3'–Deoxythymidine to 3'–Amino–3'–Deoxythymidine I Human Liver Microsomes and Its Relationship to Cytochrome P–450," *Clin. Pharmacol. Ther.* (1993) 54:168–176 (Issue No. 2, Aug., 1993).

Plunkett, W. et al., "Modulation of 9–β–D–Arabinofuranosyladenine–5'–Triphosphate and Deoxyadenosine–Triphosphate in Leukemic Cells by 2'–Deoxycoformycin During Therapy with 9–β–D–Arabinfuranosyladenine," *Cancer Res.* (1982) 42(5):2092–2096 (May, 1982).

Quiggle et al., "Design of New Photoafinity Lables for Ribosomal Peptidyltransferase," *Biochemsitry*, 17(I):94–101 (Jan., 1978).

Ratsep et al., "8–Diazoguanosine, 2,8–Diaminoadenosine and Other Purine Nucleosides Derived from Guanosine," *Nucleosides Nucleotides*, 9(8):1001–1013 (1990); only Abstract supplied.

Reist, E.J. et al., "Potential Anticancer Agents. LXXVI. Synthesis of Purine Nucleosides of β–D–Arabinofuranose," *J. Org. Chem.*, (1962) 27:3274–3279 (Sep., 1962).

Resegotti, L., "Treatment of Acute Non–Lymphoid Leukemia (ANLL) in elderly patients. The Gimema Experience," *Leukemia* (1992) 6(suppl. 2):72–75.

Riquelme et al., "Conformational and Allosteric Changes in Furctose 1,6–Bisphosphate Upon Photoaffinity Labeling with 2–Azidoadenosine Monophosphate," *J. Biological Chemistry* 258(13):8240–8245 (Jul. 10, 1983).

Robins et al. (I), "Nucleic Acid Related Compounds. 33 . . . ," *Canadian Journal of Chemistry* 59(17):2601–2607 (Sep. 1, 1981).

Robins et al.(II), "The Synthesis of 2–, 6–, and 2, 6–Halogens Substituted 9–(2, 3, 5–tri–O–acetyl–β–D–ribofuranosyl)purines," in *Nucleic Acids Research Symposium Series No. 9*, A. E. Pritchard (ed.), Bechyne Castle, Czechoslovakia, Sep. 6–11, 1981, pp. 61–63.

Robins, M.J. and Bason, G.L., "6–Chloro–9–(2–deoxy–β–D–erythro–pentofuranosyl)purine from the Chlorination of 2'–deoxyinosine," In: *Nucleic Acid Chemistry*; Townsend, L.B.; Tipson, R.S., Eds.; John–Wiley & Sons: New York (1978) Part II, pp. 601–606.

Rocci, M.L. Jr. and Jusko, W.J., "LAGRAN Program for Area and Moments in Pharmacokinetic Analysis," *Comp. Prog. Biomed.* (1983) 16(3):203–216.

Roy et al., "8–Azidoadenosine and Ribonucleotide Reductase," *Biochemical and Biophysical Research Communications*, 187(1):432–437 (1992); only abstract supplied.

Seiter et al., "Synthesis of Novel Spin–Labeled Photoaffinity Derivatives of NAD+ and ATP and Their Characterization as Coenzymes and Substrates of Several Enzymes," *Synthesis*, Issue No. 2, 269–273 (Feb., 1996).

Schulze, P. and Sönnichsen, "the Management of Herpes Zoster Infections," (1993) *Virus & Life*, 13–16 (Sep., 1993).

Shanmuganathan, K. et al., "Enhanced Brain Delivery of an Anti–HIV Nucleoside 2'–F–ara–ddI by Xanthine Oxidase Mediated Biotransformation," *J. Med. Chem.* (1994) 37:821–827.

Stula, D. and Lyrer, P., "Severe Herpes simplex Encephalitis: Course 15 Years Following Decompressive Craniotomy," *Schweiz. Med. Wochenschr.* (1992) 122:1137–1140 (*English Abstract Only*) (Jul. 25, 1992).

Suzuki, Y. et al., "Cytomegalovirus Encephalitis in Immunologically Normal Adults," *Rinsho. Shinkeigaku* (1990) 30:168–173 (*English Abstract Only*) (Feb., 1990).

Svendsen, K.R. et al. (1992), "Toxicity and Metabolism of 3'–deoxyadenosine N'–oxide in Mice and Ehrlich Ascites Tumor Cells," *Cancer Chemother. Pharmacol.* (1992) 30:86–94.

Tartaglione, T.A. et al., "Principles and Management of the Acquired Immunodeficiency Syndrome," In: *Pharmacotherapy. A Pathophysiologic Approach*, J.T. DiPiro et al. (Eds.) Appleton and Lange, Norwalk, CN (1993) 1837–1867 (Chapter 112).

Tritsch, G.L. et al., "Synergism Between the Antiproliferative Activities of Arabinosyladeniine and $N_6$–Benzoyladenosine," *Cancer Biochem. Biophys.* (1977) 2(2):87–90.

Tuntland, T. et al., "Afflux of Zidovudine and 2',3'–dideoxyinosine out of the Cerebrospinal Fluid when Administered Alone and in Comination to Macaca Nemestina," *Pharm. Res.* (1994) 11:312–317 (Issue No. 2).

Vinayak et al., "Nucleic Acid Related Compounds. 81 . . . ," *Journal of Heterocyclic Chemistry* 30(5), 1181–1189 (Oct.–Nov., 1993).

Weigend et al., "Fluorescent Guanosine Nucleotide Analogs Suitable for Photoaffinity–Labeling Expreiments," *European J. Biochemistry* 65(2):473–479 (1976): *Chemical Abstracts* 85(7), p. 189 Abstract No. 42417b (Aug. 16, 1985), only abstract supplied.

Wetzel, R. and Eckstein, F., "Synthesis and Reactions of 6–Methylsulfonyl–9–β–D–ribofuranosylpurine," *J. Org. Chem.* (1975) 40(5):658–660.

Whitley, R.J., "Neonatal Herpes Simplex Virus Infections," *J. Med. Virol.* (1993), Suppl. 1, 13–21.

Whitley, R.J., "Herpes Simplex Virus Infections of the Central Nervous System. Encephalitis and Neonatal Herpes," *Drugs* (1991) 42:406–427 (Issue No. 3).

Whitley, R.J., "Vidarabine: A Preliminary Review of its Pharmacological Properties and Therapeutic Use," *Drugs* (1980) 20:267–282.

Wower et al., "Synthesis of 2,6–Diazido–9–(β–D–ribofuranosyl)purine 3', 5'–Bisphosphate: Incorporation Into Transfer RNA and Photochemical Labeling of *Escherichia coli* Ribosomes," *Bioconjuate Chemsitry* 5(2), 158–161 (Mar.–Apr. 1994).

Yang, T.Y. et al., "Studies on Pharmacokinetics of 9–(β–D–arabinosyladenine Nanocapsules," *Yao. Hsueh. Hsuech. Pao.* (1992) 27(12):923–927 (*English Abstract Only*).

Yao–Zhong Xu, "Post Synthetic Introduction of Labile Functionalities onto Purine Residues via 6–Methylthiopurines in Oligodeoxyribonucleotides," *Tetrahedron*, 52(32), 10737–10750 (Aug. 5, 1996).

Yener, K. et al., "Cordycepin Selectively Kills TdTpPositive Cells," Abstract of (p. 119) Presentation to American Soc. Of Clin. Oncology Meeting vol., 12, 276, Mar. 1993.

Yuan, J., "Estimation of Variance of AUC in Animal Studies," *J. Pharm. Sci.* (1993) 82(7) 761–763 (Jul. 1993).

* cited by examiner

THERAPEUTIC AZIDE COMPOUNDS

CROSS-REFERENCE TO RELATED APPLICATIONS

This application is a division of application Ser. No. 09/033,996, filed Mar. 3, 1998, now U.S. Pat. No. 6,271,212, is a continuation of PCT International Application No. PCT/US96/14494, Sep. 6, 1996, which claims priority from Provisional Application No. 60/003,383, filed Sep. 7, 1995.

GOVERNMENT RIGHTS

This invention was funded, at least in part, by the U.S. Government under National Institutes of Health Grant No. AI25899. Accordingly, the U.S. Government may have certain rights herein.

FIELD OF THE INVENTION

This invention is in the field of pharmaceuticals, specifically azide derivatives of pharmaceutically active compounds.

BACKGROUND OF THE INVENTION

In recent years the pharmaceutical industry has developed an effective panoply of therapeutic compounds for the treatment of human disease. Antibacterial compounds such as penicillin, the sulfa drugs, and more recently, aminoglycocide and cephalosporin antibiotics have drastically reduced fatalities from bacterial infection. Viral infections, once thought to be beatable, can now be controlled with antiviral agents, notably nucleoside analogs such as acyclovir and related compounds. A diagnosis of cancer, at one time a virtual death sentence, is now simply a prelude to often-successful treatment with antineoplastic drugs such as methotrexate. Even epilepsy, whose victims were thought to have been chosen by the gods as special vehicles of divine possession, has yielded to the protection of dopantine. AIDS itself, the newest and most frightening of our diseases, has been at least retarded in its progress by nucleoside replication inhibitors such as AZT (3'-azido-3'-deoxythymidine).

Effective as these pharmaceuticals are, however, once inside the patient's body, many are quickly inactivated by degrading enzymes, particularly deaminases. In some cases, for example when it is necessary for the active drug to cross the blood-brain barrier, undesirably large doses of the drug must be administered in order to ensure enough will remain in circulation long enough to reach the brain in therapeutic quantities. In other cases, drugs must be administered continuously, effectively tying the patient to the iv needle, in order to provide enough active form of the drug in circulation without having to administer toxically high concentrations.

It is thus desirable to provide therapeutic compounds in a form which will persist for a longer time in the patient's body without degrading than drugs currently in use.

A number of efforts have been made to improve these effective pharmaceuticals by increasing their lipophilicity by attaching lipophilic groups such as acetyl or even cholesterol so as to allow faster penetration into intercellular spaces and compartments with lipophilic barriers, such as the blood-brain barrier. However, these measures have not always been as effective as desired.

One class of particularly effective antiviral pharmaceuticals which has been used in the treatment of herpes viruses as well as other viruses, particularly in immunocompromised patients such as those infected with the AIDS virus, are nucleoside analogs. These analogs, after phosphorylation by the enzymes of the cell, disrupt DNA synthesis and are thus useful as anticancer agents as well as inhibitors of virus multiplication. One of the early compounds used for this purpose was 5-iodo-2'-deoxyuridine (IDU). [Darby, G. (1995), "In search of the perfect antiviral," Antiviral Chem. & Chemother. 1:54–63]. This article discloses that such drugs also tend to be toxic to normal cells due to the fact that they inhibit DNA replication. Acyclovir and valaclovir are mentioned as particularly useful compounds in this regard because they become phosphorylated only within infected cells, and thus inhibit DNA replication only in these cells. These drugs, however, have low oral bioavailability (15–20%), which limits their usefulness. Again, a method for increasing the half-lives of such drugs is needed.

Vidarabine, 9-($\beta$-D-arabinofuranosyl)adenine (ara-A) was originally discovered as an antitumor agent [Reist, E. J. et al., "Potential anticancer agents. LXXVI. Synthesis of purine nucleosides of $\beta$-D-arabinofuranose," J. Org. Chem. (1962) 27:3274–3279] and in later studies, it was shown to be active against herpes simplex virus type 1 and 2 [Drach, J. C. and Shipman, C. Jr., "The selective inhibition of viral DNA synthesis by chemotherapeutic agents: an indicator of clinical usefulness?" Ann. NY Acad Sci (1977) 284:396–409; Andrei, G. et al., "Comparative activity of various compounds against clinical strains of herpes simplex virus," Eur. J. Clin. Microbiol. Infect. Diseases (1992) 11:143–151]. Ara-A is a licensed compound for the treatment of herpes simplex keratitis [Denis, J. et al., "Treatment of superficial herpes simplex hepatitis with Vidarabine (Vira A): A multicenter study of 100 cases," J. Fr. Ophthalmol. (1990) 13:143–150] and encephalitis [Whitley, R. J., "Herpes simplex virus infections of the central nervous system. Encephalitis and neonatal herpes," Drugs (1991) 42:406–427; Stula, D. and Lyrer, P., "Severe herpes simplex encephalitis: Course 15 years following decompressive craniotomy," Schweiz. Med. Wochenschr. (1992) 122:1137–1140; Whitley, R. J., "Neonatal herpes simplex virus infections," J. Med. Virol. (1993), Suppl. 1, 13–21]. It has also been considered for the treatment of genital and disseminated herpes infections [DRUGDEX (R) Information System, Gelman, C. R. and Rumack, B. H., Eds.; MicroMedex, Inc., Englewood, Colo., 84, Expired May 31, 1995], cytomegalovirus encephalitis [Suzuki, Y. et al., "Cytomegalovirus encephalitis in immunologically normal adults," Rinsho. Shinkeigaku (1990) 30: 168–173], chronic hepatitis B virus (HBV) infection [Chien, R. N. and Liaw, Y. F., "Drug therapy in patients with chronic type B hepatitis," J. Formos. Med. Assoc. (1995) 94(suppl. 1):s1–s9; Fu, X. X., "Therapeutic effect of combined treatment with ara-A, dauricine and Chinese herbs in chronic hepatitis B infection," Chung. Hua. Nei. Ko. Tas. Chih. (1991) 30:498–501] and acute non-lymphoid leukemia [Resegotti, L., "Treatment of acute non-lymphoid leukemia (ANLL) in elderly patients. The GIMEMA experience," Leukemia (1992) 6 (suppl. 2):72–75]. Ara-A may also be an alternative therapy for acyclovir-resistant herpes simplex virus, cytomegalovirus and varicella-zoster virus infections [Chatis, P. A. and Crumpacker, C. S., "Resistance of herpes viruses to antiviral drugs," Antimicrob. Agents Chemother. (1992) 36:1589–1595; Nitta, K. et al., "Sensitivities to other antiviral drugs and thymidine kinase activity of acyclovir-resistant herpes simplex virus type 1," Nippon. Ganka. Gakkai. Zasshi (1994) 98:513–519]. However, the use of ara-A as a clinically effective agent is limited due to its rapid deamination to ara-H by adenosine deanmnase (ADA) in vivo [Cass, E. C., "9-$\beta$-D-Arabinofuranosyladenine (Ara- A)," In *Antibiotics. Mechanism of Action of Anti-eukaryotic and Antiviral Compounds*; Hahn, F. E., Ed.; Springer-Verlag: New York (1979) V:87–109; Whitley, R. et al., "Vidarabine: a preliminary review of its pharmacological properties and therapeutic use," Drugs (1980) 20:267–282] as well as its poor solubility in water.

There were several attempts to prevent the rapid metabolism of ara-A [Plunkett, W. and Cohen, S. S., "Two approaches that increase the activity of analogs of adenine nucleosides in animal cells," Cancer Res. (1975) 35:1547–1554], including the co-administration of adenosine deaminase inhibitors such as deoxycoformycin [Cass, C. E. and Ah-Yeung, T. H., "Enhancement of 9-β-D-arabinofuranosyladenine cytotoxicity to mice leukemia L1210 in vitro by 2'-deoxycoformycin," Cancer Res. (1976) 36:1486–1491; LePage, G. A. et al., "Enhancement of antitumor activity of arabinofuranosyl adenine by 2'-deoxycoformycin," Cancer Res. (1975) 36(4): 1481–1485; Cass, C. E. et al., "Antiproliferative effects of 9-β-D arabinofuranosyladenine-5'-monophosphate and related compounds in combination with adenosine deaminase inhibitors against a mouse leukemia L1210/ C2 cells in culture," Cancer Res. (1979) 39(5):1563–1569; Plunkett, W. et al., "Modulation of 9-β-D-arabinofuranosyladenine-5'-triphosphate and deoxyadenosine-triphosphate in leukemic cells by 2'-deoxycoformycin during therapy with 9-β-D-arabinfuranosyladenine," Cancer Res. (1982) 42(5): 2092–2096; Agarwal, R. P. et al., "Clinical pharmacology of 9-β-D-arabinofuranosyladenine in combination with 2'-deoxycoformycin," Cancer Res. (1982) 42(9): 3884–3886] and $N^6$-benzoyladenosine [Tritach, G. L. et al., "Synergism between the antiproliferative activities of arabinofuranosyladenine and $N^6$-benzoyladenosine," Cancer Biochem. Biophys. (1977) 2(2):87–90]. The effects of ara-AMP and ara-A in combination with erythro-9-(2-hydroxy-3-nonyl)adenine (EHNA) were studied in mouse leukemia L1210/ C2 cell culture and the results were promising [Cass, C. E. et al., "Antiproliferative effects of 9-β-D arabinofuranosyladenine-5'-monophosphate and related compounds in combination with adenosine deaminase inhibitors against a mouse leukemia L1210/ C2 cells in culture," Cancer Res. (1979) 39 (5):1563–1569]. However, in the clinical trials with the combination of ara-A and deoxycoformycin some patients developed toxicities [Miser, J. S. et al., "Lack of significant activity of 2'-deoxycoformycin alone or in combination with adenine arabinoside in relapsed childhood acute lymphoblastic leukemia. A randomized phase II trial from children's cancer study group," Am. J. Clin. Oncol. (1992) 15:490–493]. Other approaches comprise the conjugation of ara-AMP to lactosaminated human serum albumin [Jansen, R. W. et al., "Coupling of antiviral drug ara-AMP to lactosaminated albumin leads to specific uptake in rat and human hepatocytes," Hepatology (1993) 18:146–152] and administration of ara-A in nanocapsules to improve the pharmacokinetic profiles [Yang, T. Y. et al., "Studies on pharmacokinetics of 9-β-D-arabinosyladenine nanocapsules," Yao. Hsueh. Hsuech. Pao. (1992) 27:923–927]. 9-(β-D-Arabinofuranosyl)-6-dimethylaminopurine (ara-DMAP), after its intravenous administration in rats and monkeys, was rapidly converted to 9-(β-D-arabinofuranosyl)-6-methylaminopurine (ara-MAP) and other purine metabolic end products [Koudriakova, T. et al., "In vitro and in vivo evaluation of 6-azido-2'-3'dideoxy-2'-fluoro-β-D-arabinofuranosylpurine (FAAddP) and 6-methyl-2',3'-dideoxy-2'-fluoro-β-D-arabinofuranosyladenine (FMAddA) as prodrugs of the anti-HIV nucleosides, 2'-F-ara-ddA and 2'-F-ara-ddI," J. Med. Chem. In Press]. However, less than 4% of the dose of ara-DMAP was found to be converted to ara-A and the half-life of ara-A was four times longer.

Recently, in a metabolic study of AZT, Sommadossi et al. [Cretton, E. M. and Sommadossi, J-P, "Reduction of 3'-azido-2',3'-dideoxynucleosides to their 3'-amino metabolite is mediated by cytochrome P450 and NADPH-cytochrome P-450 reductase in rat liver microsomes," Drug Metab. Dispos. (1993) 21:946–950; Wetze, R. and Eclstome, E., "Synthesis and reactions of 6-methylsulfonyl-9-β-D-ribofuranosylpurine," J. Org. Chem. (1975) 40(5):658–660] have shown that the azide moiety in AZT is reduced to an amino moiety by the cytochrome-P 450 reductase system.

Didanosine (ddI) is a synthetic nucleoside analogue structurally related to inosine with proven activity against human immunodeficiency virus (HIV) [Faulds, D. and Brogden, R. N., "Didanosine: a review of its antiviral activity, pharmacokinetics properties and therapeutic potential in human immunodeficiency virus infection, " Drugs (1992) 44:94–116]. It is approved for use in patients who are intolerant to zidovudine (AZT) or who have deteriorated on zidovudine therapy. However, its various side effects [Tartaglione, T. A. et al., "Principles and management of the acquired immunodeficiency syndrome. In: *Pharmacotherany. A pathophysiologic approach*, J. T. DiPiro et al. (Eds.) Appleton and Lange, Norwalk, Conn. (1993) 1837–1867), chemical instability in gastric acid and low oral bioavailability of 27–36% (Drusano, G. L. et al., "Impact of bioavailability on determination of the maximal tolerated dose of 2',3'-dideoxyinosine in phase I trials," Antimicrob. Agents Chemotherapy (1992) 36:1280–1283] limit its usefulness. Furthermore, there is evidence that ddI enters the central nervous system and the cerebrospinal fluid (CSF) less readily than does AZT. The extent of ddI uptake in brain tissue and CSF, relative to that in plasma, was only 4.7 and 1.5%, respectively [Collins, J. M. et al., "Pyrimidine dideoxyribonucleosides: selectivity of penetration into cerebrospinal fluid," J. Pharmacol. Exp. Ther. (1988) 245:466–470; Anderson, B. D. et al., "Uptake kinetics of 2',3'-dideoxyinosine into brain and cerebrospinal fluid of rats: intravenous infusion studies," J. Pharmacol. Exp. Ther. (1990) 253:113–118; Tuntland, T. et al., "Afflux of Zidovudine and 2',3'-dideoxyinosine out of the cerebrospinal fluid when administered alone and in combination to Macaca nemestina," Pharm. Res. (1994) 11:312–317].

In an effort to overcome the instability of ddI and 2',3'-dideoxyadenosine (ddA) in acidic conditions, the 2'-fluoro-β-D-arabinofuranosyl derivatives 2'-F-ara-ddI and 2'-F-ara-ddA of the nucleosides have been synthesized [Marquez, V. E. et al., "Acid-stable 2'-fluoro purine dideoxynucleosides as active agents against HIV," J. Med. Chem. (1990) 33:978–985]. These authors reported that 2'-F-ara-ddA and 2'-F-ara-ddI were stable in acidic media and were as potent as the parent compounds in protecting CD4+ATH8 cells from cytopathogenic effects of HIV-1. However, 2'-F-ara-ddI, as well as ddI, are relatively hydrophilic and do not readily penetrate the blood-brain barrier (BBB) in mice [Shanmuganathan, K. et al., "Enhanced brain delivery of an anti-HIV nucleoside 2'-F-ara-ddI by xanthine oxidase mediated biotransformation," J. Med. Chem. (1994) 37:821–827]. Recently, applicants synthesized a more lipophilic prodrug, 2',3'-dideoxy-2-fluoro-β-D-arabinofuranosyl-purine (2'-F-ara-ddP), which was converted to the parent nucleoside, 2'-F-ara-ddI by xanthine oxidase in vivo. Pharmacokinetic studies indicated 2'-F-ara-ddP increased the delivery of 2'-F-ara-ddI to the brain in mice. The $AUC_{brain}/AUC_{serum}$ ratio for 2'-F-ara-ddI was increased to approximately 36% after oral and intravenous prodrug administration [Shanmuganathan, K. et al., "Enhanced brain delivery of an anti-HIV nucleoside 2'-F-ara-ddI by xanthine oxidase mediated biotransformation," J. Med. Chem. (1994) 37:821–827].

Cordycepin is potentially very active against tumor growth and viral replication [Yeners, K. et al., "Cordycepin selectively kills TdT-positive cells," Abstract of presentation to American Soc. of Clin. Oncology Meeting, May 1993]. However, the effectiveness of cordycepin in vivo is markedly decreased by rapid deamination. Cordycepin exhibits its biological activity through direct inhibition of viral replication through its ability to block polyadenylic acid [poly(A)] synthesis, thus interfering with processing and maturation of both cellular and viral mRNA. [Svendsen, K. R. et al. (1992), "Toxicity and metabolism of 3'-deoxyadenosine $N^1$-oxide in mice and Ehrlich ascites tumor cells," Cancer Chemother. Pharmacol. (1992) 30:86–94.] Cordycepin is phosphorylated by adenosine kinase to 3'-deoxyadenosine monophosphate, with further phosphorylation by adenylate kinase to 3'-deoxyadenosine triphosphate which exerts toxic effects due to its incorporation into RNA in lieu of ATP, thereby functioning as a chain terminator.

In vivo, however, the effectiveness of cordycepin as an antitumor agent is limited because of very rapid deamination of the compound to yield 3'-deoxyinosine which is biologically inert. That reaction is catalyzed by adenosine deaminase. [Frederiksen, S. and Klenow, H. (1975), "3-Deoxyadenosine and other polynucleotide chain terminators," In *Handbook of experimental pharmacology*, (A. C. Sartorelli and G. Johnes, Eds.) 657–669.]

The in vivo antitumor activity of cordycepin can be enhanced by administration with adenosine deaminase inhibitor 2'-deoxycoformycin (2'-DCF). Administered together, cordycepin and 2'-DCF resulted in marked inhibition of L1210 and P388 cell growth in vitro and in mice models in vivo. [Johns, D. G. and Adamson, R. H. (1976), "Enhancement of the biological activity of cordycepin (3'-deoxyadenosine) by the adenosine deaminase inhibitor 2'-deoxycoformycin," Biochem. Pharmacol. (1976) 25:1441–1444.]

Another way to avoid deamination of cordycepin is through the use of 3'-deoxyadenosine $N^1$-oxide (3'-dANO) as a prodrug. 3'-dANO is metabolically inert until it has entered a target cell that is capable of reducing 3'-dANO to cordycepin. [Svendsen, K. R. et al. (1992), "Toxicity and metabolism of 3'-deoxyadenosine $N^1$-oxide in mice and Ehrlich ascites tumor cells," Cancer Chemother. Pharmacol. (1992) 30:86–94.]

Reduction to the amine has been observed to adversely affect the bioavailability of other drugs as well. Reduction to the amine has been shown to deactivate the antitumor agent meta-azidepyrimethamine. [Kamali, F., et al. (1988), "Medicinal azides. Part 3. The metabolism of the investigational antitumor agent meta-azidepyrimethamine in mouse tissue in vitro," Xenobiotica 18:1157–1164.]

This invention provides azide compounds, preferably azide derivatives of therapeutically active substances which provide increased half-lives for the therapeutically active substances.

Azide derivatives of certain biologically active compounds have been synthesized for the purpose of optical imaging. [Nicholls, D., et al. (1991), "Medicinal azides. Part 8. The in vitro metabolism of p-substituted phenyl azides," Xenobiotica 21:935–943.]

Azide drugs such as 3'-azido-3'-deoxythymidine (AZT, also known as zidovudine) have been used in the treatment of AIDS because of their inhibition of viral replication. [Tartaglione, T. A., et al. (1993), "Principles and management of the acquired immunodeficiency syndrome. In: Pharmacotherapy. A pathophysiologic approach, DiPiro, J. T. et al., eds., Appleton and Lange, Norwalk, Colo. 1837–1867.] AZT is reduced in vivo to the corresponding amino compound. [Placidi, L., et al. (1993, "Reduction of 3'-azido-3'-deoxythymidine to 3'-amino-3'-deoxythymidine in human liver microsomes and its relationship to cytochrome P450," Clin. Phannacol. Ther. 54:168–176. This is also true of azidodideoxynucleosides. Cretton, E. M. and Sommadossi, J-P (1993), "Reduction of 2'-azido-2',3'-dideoxynucleosides to their 3'amino metabolite is mediated by cytochrome P-450 and NADPH-cytochrome P450 reductase in rat liver microsomes," Drug Metab. Dispos. 21:946–950.] The degradation product of AZT is not therapeutically effective and is, in fact, toxic. [Cretton, E. M. et al., "Catabolism of 3'-azide-3'-deoxythymidine in hepatocytes and liver microsomes with evidence of formation of 3'-amino-3'-deoxythimidine, a highly toxic catabolite for human bone marrow cells," Molec. Pharmacol. (1991) 39:258–266.]

Kumar, R., et al. (1994), "Synthesis, in vitro biological stability, and anti-HIV activity of 5-halo-6-alkoxy (or azide) -5,6-dihydro-3'-azido-3'deoxythymidine (AZT)," J. Med. Chem. 37:4297–4306, reported that 6-azide derivatives of AZT were 2–3 log units less active than AZT.

An azide derivative of 2,6-diaminopurine as well as several other derivatives of 2,6-diaminopurine have also been recognized as potent inhibitors of HIV replication. These compounds also inhibit adenosine deaminase and inhibit the deamination of 9-beta-D-arabinofuranosyladenine (araA). [Balzarini, J. and DeClercq, E. (1989), "The antiviral activity of 9-beta-D-arabinofuranosyladenine is enhanced by the 2',3'-dideoxyriboside, the 2',3'-didehydro-2',3'-dideoxyriboside and the 3'-azido-2',3'-dideoxyriboside of 2,6-diaminopurine," Biochem. Biophys. Res. Commun. 159:61–67.]

A method as provided herein, is needed for increasing the half-life of pharmaceutically active compounds so as to avoid problems associated with the rapid degradation of the compounds in the patient's body.

SUMMARY OF THE INVENTION

This invention provides pharmaceutical compositions which comprise azide compounds, preferably azide derivatives of biologically active therapeutic compounds (also referred to herein as "drugs"). The azide derivatives of this invention are reduced in vivo to the corresponding drug.

Many therapeutic compounds are quite effective, but do not persist in the system as long as desired to produce the best effect. Drugs comprising amine moieties are susceptible to deamination in the body, which often destroys their effectiveness. When the amine moieties of these drugs are converted to azide ($N_3$) moieties, the azides are reduced to the corresponding amines, thus converting the azide derivatives to the active amine drugs, such that the active forms of the drug have a longer half life, continuing to exhibit biological activity in the in vivo system for a longer period of time after administration than the drugs themselves. Drugs which are ketones or have hydroxy substituents may also advantageously be converted to the corresponding azides to increase their half-lives.

In addition to having increased half-lives, azide derivatives often are better able to penetrate the cells and compartments with lipophilic barriers, such as the prostate capsule and blood-brain barrier, so that they are more effective in reaching the site where their activity is desired than the corresponding amine, ketone or hydroxy form of the drug. The azide derivatives of therapeutically active substances of this invention are sometimes referred to herein as "prodrugs" for the drugs of which they are derivatives.

As an example of this invention, the azide derivative of cordycepin, an active anticancer agent, has been prepared. $N^6$-azido-β-D-3'-deoxyribofuranosyl purine (ADRP), having an azide group in place of the amine group of cordycepin, is reduced in vivo to cordycepin, an active anticancer agent. Thereafter, the cordycepin is further deaminated to the inactive 3'-deoxyinosine metabolite:

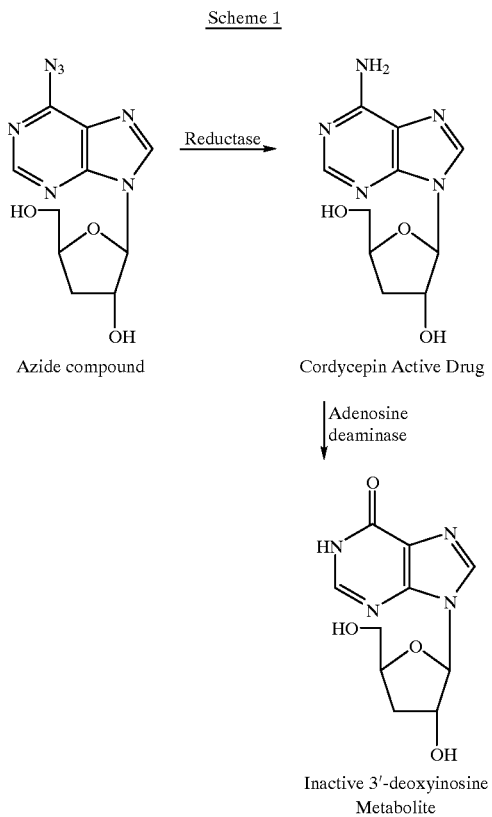

In addition, drugs which in their active form have a carbonyl moiety may be converted to the corresponding azides. The body reduces these to the corresponding amines, then further reduces them to the active carbonyl form by deaminases in vivo. For example, the corresponding azide of 2'-fluoro-2',3'-dideoxyinosine (2'-F-ara-ddI), namely 6-azido-2',3'-dideoxy-2'-fluoro-β-D-arabinofuranosylpurine (FAAddP), has been prepared. When this azide derivative is introduced into the body, it is first reduced to the corresponding amine, 2'-fluoro-2',3'-dideoxyadenosine (2'-F-ara-ddA) which is inactive, then deaminated to the active carbonyl form, 2'-F-ara-ddI:

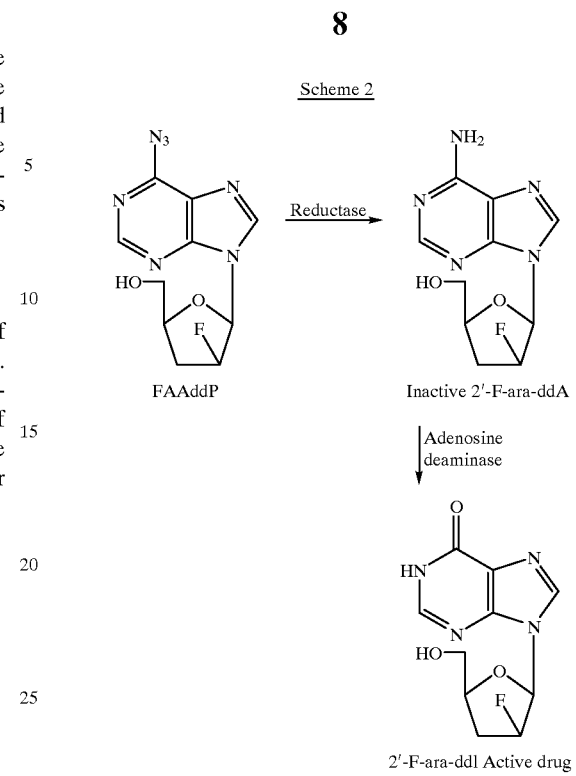

Drugs having a hydroxy form may similarly be administered as azide derivatives which are reduced in vivo first to the amine, then the hydroxy form. For example, (−)-β-D-2,6-amino-azidopurine dioxolane (DAPD) is reduced to the diamino derivative which is then deaminated to the corresponding hydroxy form, (−)-β-D-Dioxolane guanine (DXG):

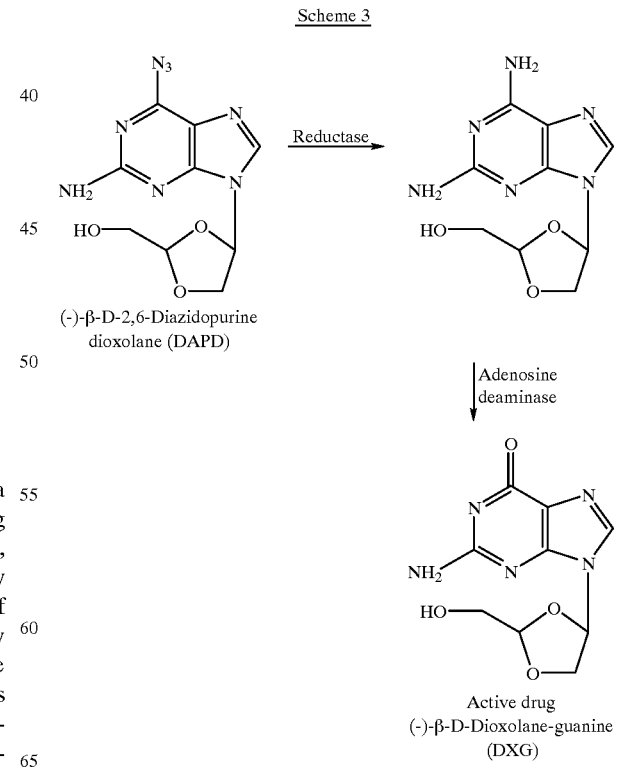

Preferably, the drugs converted to azides herein are drugs having primary amine ring substituents, which are capable of being reduced from the azide to the corresponding amine. Other preferred drugs are aliphatic amines, drugs having secondary or tertiary amine ring or chain substituents, drugs with oxygen substituents attached to carbon atoms (i.e. ketones) or hydroxy substituents attached to carbon atoms, which are capable of being reduced from the azide to the corresponding amine, and from the amine to the ketone or hydroxy form.

Accordingly, this invention provides a pharmaceutical composition comprising:
  a) an azide derivative of a drug, said azide derivative being capable of being converted to the drug in vivo;
  b) a suitable pharmaceutical carrier.

Azides which are capable of being converted to the corresponding amines in vivo include azides corresponding to aryl, ring-substituted aryl, and aliphatic amines, preferably primary amines, and azides corresponding to drugs having carbonyl or hydroxy groups, such as oxygen substituted aryl and aliphatic compounds.

These azides are selected from the group consisting of azide derivatives of biologically active purines and pyrirnidines, nucleoside analogs, phosphorylated nucleoside analogs, aminoglycoside antibiotics, ampicillin and ampicillin analogs, sulfonamides, cephalosporin and cephalosporin analogs, and other alicyclic amines, ketones, and hydroxy compounds, including aralkyl, heterocyclic aralkyl, and cyclic aliphatic compounds, where the amine or oxygen moiety is on the ring, or where the amine or oxygen moiety is on an aliphatic side chain.

The most preferred compounds of this invention are 2'-F-azido-ara-ddP, an azide derivative of 2'-F-ara-ddI; 9-(β-D-arabinofaranosyl)-6-azidopurine (6-AAP) an azide derivative of adenine arabinoside (AraA); and $N^6$-azido-β-D-3'-deoxyribofuranosyl purine, an azide derivative of cordycepin.

This invention also provides a method of increasing the half-life of a drug in a subject comprising administering to the subject an azide derivative of said drug capable of being reduced to the drug in the patient's body. Following administration of the azide derivative, the patient's serum levels may be monitored to determine the presence of the drug, or specific effects of the drug may be monitored.

The methods of this invention also include a method for ameliorating a pathological condition in a patient comprising treating the patient with a therapeutically effective azide compound, preferably one which is capable of metabolizing in vivo to a therapeutic compound effective for the treatment of said pathological condition. This method also includes co-administering said azide compound with other therapeutic agents.

Azides are converted by reductase in the subject's body to the corresponding amines, and are then further deaminated. There are a number of deaminases in the body, including adenosine deaminase and cytidine deaminase, which are capable of further metabolizing amines to the corresponding ketones or hydroxy-substituted compounds. The active drug may be the amine, or the ketone or hydroxy compound.

BRIEF DESCRIPTION OF THE FIGURES

FIG. 1 shows pharmacokinetic profiles of the azide derivative of cordycepin, $N^6$-azido-β-D-3'-deoxyribofuranosyl purine, cordycepin and metabolite after oral (●) and intravenous (∇) administration of the azide derivative to mice at a dose of 100 mg/kg.

DETAILED DESCRIPTION OF THE PREFERRED EMBODIMENTS

Figure 1A:
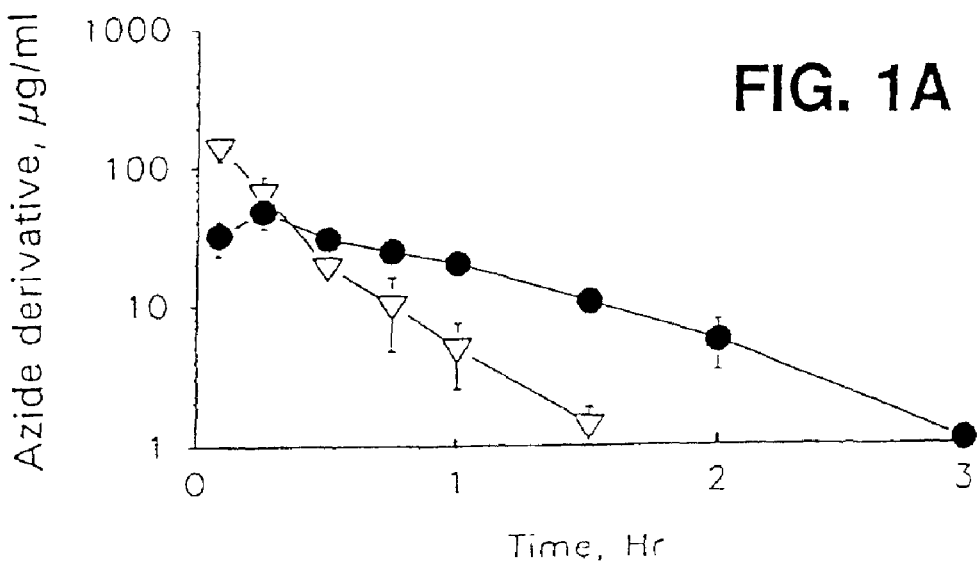
FIG. 1A shows the profile for the azide derivative.

A preferred class of the azide derivatives of this invention are azide derivatives of biologically active purines and pyrimidines, nucleoside analogs, and phosphorylated nucleoside analogs. For example, azide derivatives are prepared from the following drugs: dideoxyinosine (ddI), for which the azide derivative is 6-azido-(2',3'-dideoxy-β-D-glycero-pentofuranosyl) purine; 2'-F-ara-ddI, for which the corresponding azide derivative is 6-azido-2',3'-dideoxy-2'-fluoro-β-D-arabinofuranosylpurine (FAAddP); arabinofuranosyladenine (araA), for which the corresponding azide derivative is 9-(β-D-arabinofuranosyl)-6-azidopurine (6-AAP); cordycepin, for which the corresponding azide derivative is $N^{6\text{-}}$azido-β-D-3'-deoxyribofuranosyl purine; flucytosine for which the corresponding azide derivative is 4-azido-5-fluoro-2(1H)-pyrimidinone; cytarabine, for which the corresponding azide derivative is 4-azido-1-β-D-arabinofuranosyl-2(1H)-pyrimidinone; 1-(fluoroarabino) fluorocytosine, for which the corresponding azide derivative is 4-azido-5-fluoro-1-(β-D-arabinofuranosyl-2(1H)-pyrimidinone; trimethoprim, for which the corresponding azide derivative is 2,4-diazido-5-(3,4,5-trimnethoxybenzyl) pyramidine; 1-(fluoroarabino)fluorocytosine, for which the corresponding azide derivative is 4-azido-5-fluoro-1-β-D-arabinofuranosyl-2(1H)-pyrimidinone; arabinocytidine, for which the corresponding azide derivative is 4-azido-1-β-D-ribofuranosyl-2-(1H-pyrirndinone; and 2-chloro-9-arabinodeoxyadenosine, for which the corresponding azide derivative is 2-chloro-6-azido-5-arabinopurine; and purine-derived antibiotics such as acyclovir, for which the corresponding azide derivative is 2-amino-6-azido-1,9-dihydro-9[(2-hydroxyethoxy)methyl]-purine; penciclovir, for which the corresponding azide derivative is 2-amino-6-azido-1,9-dihydro-9-[dihydroxymethyl]propyl-purine; and ganciclovir for which the corresponding azide derivative is 2-amino-6-azido-1,9-dihydro-9-[dihydroxymethylmethoxymethyl]-purine.

A preferred class of nucleoside analogs are the nucleoside analogs used as antivirals, for example in the treatment of herpes simplex virus (HSV), including the pyrimidine nucleoside analogs idoxuridine (IDU), trifluorothymidine ($F_3T$), and the purine nucleoside analogs vidarabine, acyclovir, valaciclovir, ganciclovir, penciclovir, and famciclovir.

A further preferred class of nucleoside analogs includes the foregoing along with β-D-5-Fluoro-1',3'-dioxalane cytosine (β-D-FDOC), β-D-5-Fluoro-2',3'-dideoxycytidine (β-D-FddC), β-D-5-Fluoro-2',3'-dideoxy-2',3'-didehydrocytosine (β-D-Fd4C), β-D-5-Fluoro-3'deoxy-3'thiacytidine (β-D-FTC), adenosine, 2'-deoxyadenosine, cytidine, 2'-deoxycytidine, 5'-fluorocytosine, and arabinofuranosylcytosine (ara-C), all of which are converted to the corresponding azide by treatment with the appropriate azide donor, e.g. $N_3$.

Monophosphates, diphosphates and triphosphates of the azide derivates of nucleoside analogs also constitute a preferred class of compounds of this invention.

Another preferred class of azide derivatives are azide derivatives of aminoglycoside antibiotics which are primary amines, ketones, or hydroxy-substituted compounds, such as gentamycin, tobramycin and kanamycin.

A further preferred class of azide derivatives are azide derivatives of ampicillin and its analogs such as bacampicillin, for which the corresponding azide derivatives are 6-[(azidephenylacetyl) amino]-3,3-dimethyl-7-oxo-4-thia-1-azabicyclo-[3.2.0]heptane-2-carboxylic acid and ester, respectively.

A further preferred class of azide derivatives are azide derivatives of sulfonamides which are primary amines or ketones, such as p-azidebenzenesulfonamide and its analogs. Azide derivatives can be synthesized by means known to the art corresponding to the following sulfa drugs: sulfabenz, sulfabenzamide, sulfabromomethazine, sulfacetamide, sulbenox, sulfacytine, sulfadiazine, sulfadicramide, sulfadimethoxine, sulfadoxine, sulfaethidole, sulfaaguanidine, sulfaguanole, sulfalene, sulfamerazine, sulfameter, sulfamethazine, sulfamethomidine, sulfamethoxazole, sulfamethoxypyridazine, sulfametrole, sulfamidochrysoidine, sulfamoxole, sulfanilamide, sulfanilamidomethanesulfonic acid triethanolate, sulfanilamidosalicylic acid, sulfanilic acid, 2-p-sulfanilyanilinoethanol, p-sulfanilylbenzylamine, sulfanilyl urea, N-sulfanilyl-3,4-xylamide, sulfanitran, sulfaperine, sulfaphenazole, sulfaproxyline, sylfapyridine, sulfaquinoxaline, sulfasomizole, sulfasymazine, sulfathiazole, sulfaathiourea, sulfazamet, 4,4'-sulfinyldianiline, sulfisomidine and sulfisoxazole.

A further preferred class of azide derivatives are azidephenyl derivatives of cephalosporin or its biologically active analogs which are primary amines or ketones, such as cephalexin, for which the corresponding azide derivative is [7-[azidephenylacetyl)amino-3-methyl-8-oxo-5-thia-1-azabicyclo[4.2.0]oct-2-ene-2-carboxylic acid; cephaloglycin, for which the corresponding azide derivative is 3-[(acetyloxy)methyl)-7-[(azidephenylacetyl)amino]-8-oxo-5-thia-1-azabicyclo[4.2.0]oct-2-ene-2-carboxylic acid; cephalosporin C, for which the corresponding azide derivative is 7-(D-5-azido-5-carboxyvaleramido)-3-(carboxy)-8-oxo-5-thia-1-azabicyclo[4.2.0]oct-2-ene-2-carboxyliacid; cephamycins for which the corresponding azide derivatives are 7-(D-5-azido-5-carboxyvaleramido)-7-methyloxy-3-(carboxy)-8-oxo-5-thia-1-azabicyclo[4.2.0]oct-2-ene-2-carboxylic acid esters, and cephadrine.

A further preferred class of azide derivatives are azide derivatives of biologically active alicyclic amines, ketones, and hydroxy-substituted compounds, including aralkyl, heterocyclic aralkyl, and cyclic aliphatic compounds, where the amine or oxygen moiety is on the ring, e.g. trimetrexate, for which the corresponding azide derivative is 2,4-diazido-5-methyl-6-[3,4,5-trimethoxyanilino)methyl]quinazoline; procaine, for which the corresponding azide derivative is p-azidebenzoyldiethylaminoethanol; dapsone, for which the corresponding azide derivative is 4,4'-diazidodiphenyl sulfone; amantadine, for which the corresponding azide derivative is 1-azidetricyclo[3.3.1.1$^{3,7}$]decane; and methotrexate, for which the corresponding azide derivative is N-[4-[[(2, 4-Diazido-6-pteridinyl)methyl]methylamino]benzoyl]-L-glutamic acid; or where the amine or oxygen moiety is on an aliphatic side chain, e.g. amphetamine, for which the corresponding azide derivative is 1-phenyl-2-azidepropane; L-dopa, for which the corresponding azide derivative is 2-azido-3-(3,4-dihydroxyphenyl)propanoic acid; trimethoprim, for which the corresponding azide derivative is 2,4-diazido-5-(3,4,5-trimethoxybenzyl)pyrimidine; and histamine, for which the corresponding azide derivative is β-azidoethylimidazole.

A further preferred class of azide derivatives are azide derivatives of biogenetic amines including epinephrin, norepinephrin, dopamine, and seratonin.

Corresponding azides may be formed for drugs useful for virtually any therapeutic purpose, so as to increase the half-lives of said drugs. For example, in addition to drugs which are antibacterial, antiviral, antifungal, local anesthetic and cancer therapeutic, for which examples have been given above, corresponding azides may be made for diuretics, for example, furosemide; anesthetics, for example ketamine; non-steroidal anti-inflammatories, for example 3-amino-4-hydroxybutyric acid; psychiatric drugs, for example Prozac; beta-blockers, for example propranolol; hormones, for example thyroid; and others. Suitable drugs may be identified by those skilled in the art by reviewing compilations of therapeutic compounds such as Merck's Manual, and identifying those having amine, carbonyl or hydroxy substituents. Formulation of corresponding azides may be readily accomplished by those of ordinary skill in the art without undue experimentation by means known in the art such as are described herein.

As will be appreciated by those skilled in the art, compounds having more than one amino, carbonyl, or hydroxy moiety may have all, at less than all, e.g. only one, of these substituents converted to azide groups.

The azide derivatives of therapeutic compounds claimed herein by means of their chemical names include the free forms as well as pharmaceutically acceptable salts (including esters) thereof. Depending on the physicochemical characteristics of the drug, said pharmaceutically acceptable salt may further be either inorganic acid addition salts such as hydrochloride, hydrobromide or sulfate; organic acid addition salts such as citrate, acetate, oxalate, hibenzate, methanesulfonate, alkali metal salts such as sodium salt or potassium salt, alkaline earth metal salts such as calcium salt or magnesium salt, amine salts, and the like.

The dose of the azide derivative to be used is not critical, but the azide derivative is preferably used within the usual dosage range of the drug to which it reduces. As will be appreciated by those skilled in the art, dosage amount and timing may advantageously be varied in light of the longer half-lives of the drugs when the azide derivatives are administered, as compared to the case in which the drug itself is administered.

The azide derivatives of therapeutic compounds hereof may be administered to a subject or patient which is a warm-blooded animal, including man, via any means known to the art, including intravenously, by injection, and through conventional enteral routes, for example, orally or rectally. Further these compounds may be administered in the form of conventional preparations, for example, in solid dosage forms such as tablets, pills, powders, granules or suppositories; or in liquid dosage forms such as solutions, syrups, emulsions, elixirs, suspension or lemonades. In formulating these preparations, there may be used a pharmaceutically acceptable carrier such as a binder e.g., syrup, arabic gum, gelatin, sorbit, tragacanth, polyvinylpyrrolidone, a diluent such as lactose, sucrose, corn starch, calcium phosphate, sorbit and the like, a lubricant such as magnesium stearate, talc, polyethylene glycol, silica, and the like, a disintegrator, such as corn starch, a wetting agent such as sodium lauryl sulfate, a suppository base such as cacao butter, laurin butter, polyethylene glycol, eg. macrogol, glycerinated gelatin, triglyceride of saturated fatty acids C12–D18, a flavoring agent, sweetening agent, or coloring agent. The term "pharmaceutically acceptable carrier" as used herein does not include water alone or alcohols alone, although any of the foregoing additives in combination with water may constitute a pharmaceutically acceptable carrier.

In general, azide derivatives may be prepared by means known to the art. Azide derivatives of aromatic ketones, hydroxy-substituted compounds or amines may be synthesized starting with the corresponding chloride and exchanging with sodium or lithium azide. For example, azidocytosine analogs may be prepared from uracil analogs according to the following scheme:

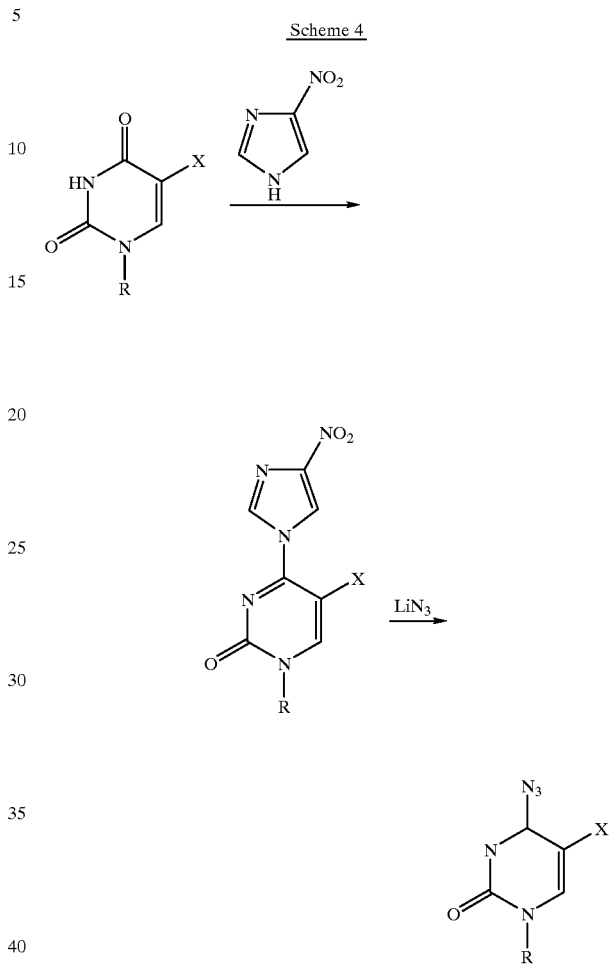

Azidoadenine analogs may be prepared from guanine analogs according to the following scheme:

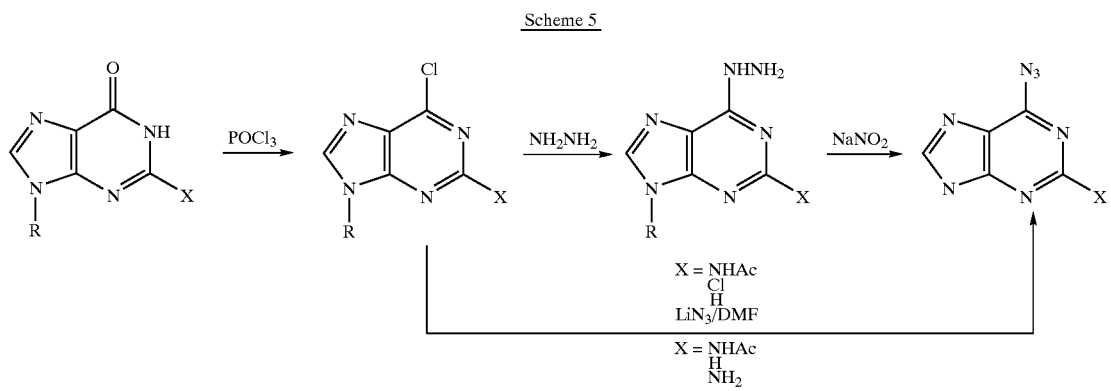

The synthesis of the azide derivative for acyclovir, 2-amino-6-azido-1,9-dihydro-9[(2-hydroxyethoxy)methyl]-purine, is shown in the following scheme:
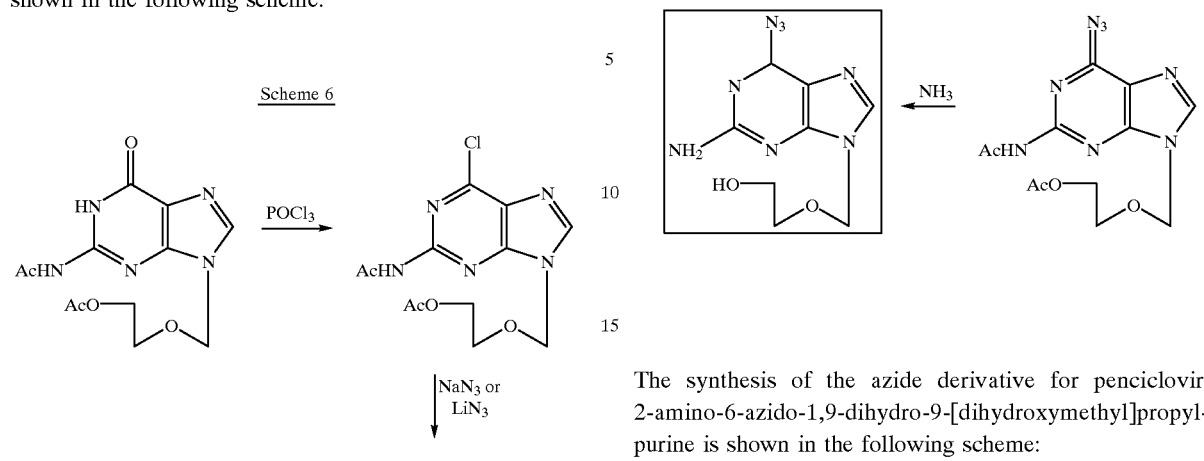
The synthesis of the azide derivative for penciclovir, 2-amino-6-azido-1,9-dihydro-9-[dihydroxymethyl]propyl-purine is shown in the following scheme:
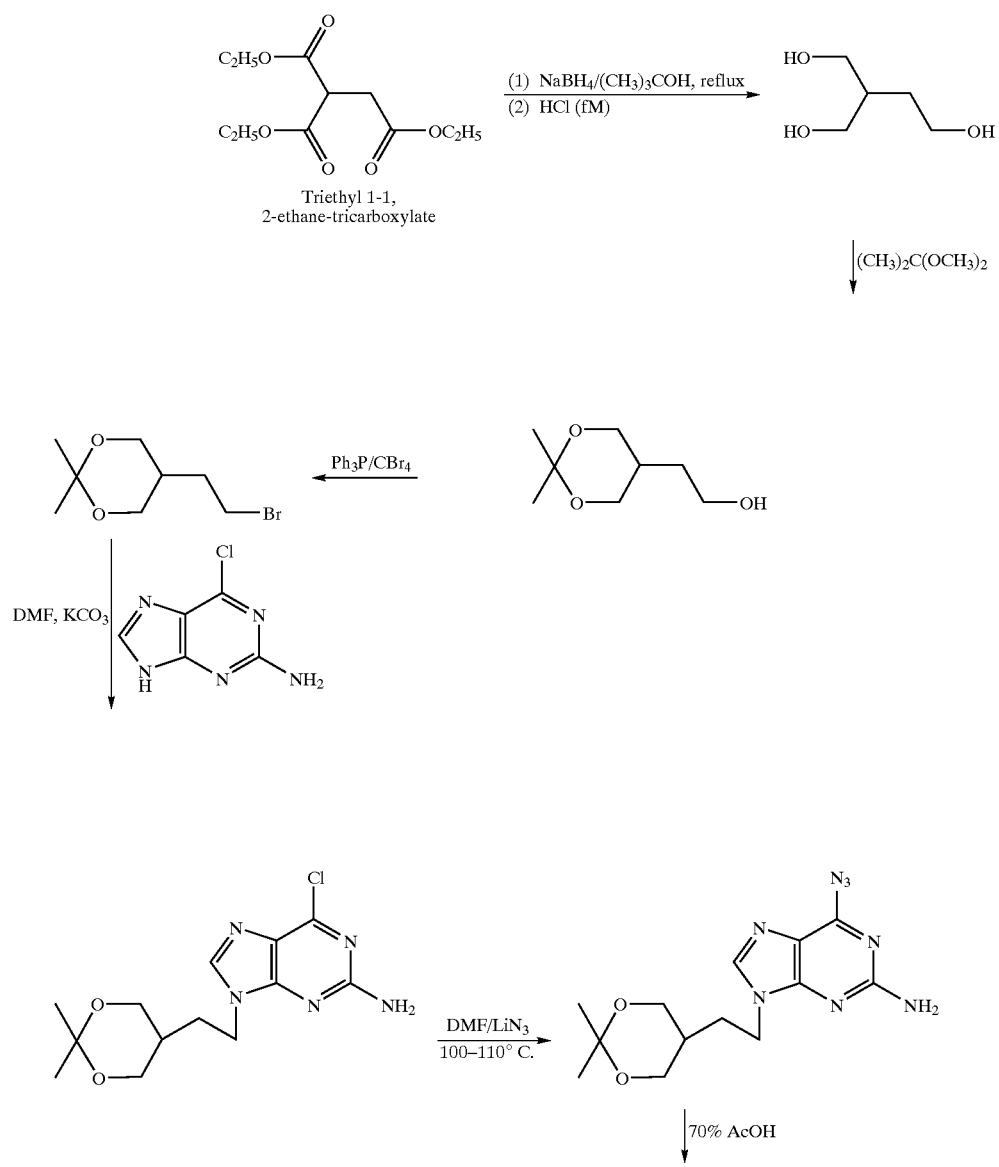

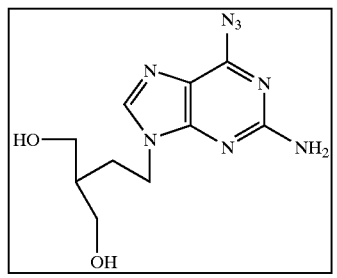

The synthesis of the azide derivative for ganciclovir, 2-amino-6-azido-1,9-dihydro-9[dihydroxymethylmethoxymethyl]-purine, is shown in the following scheme:

Scheme 8

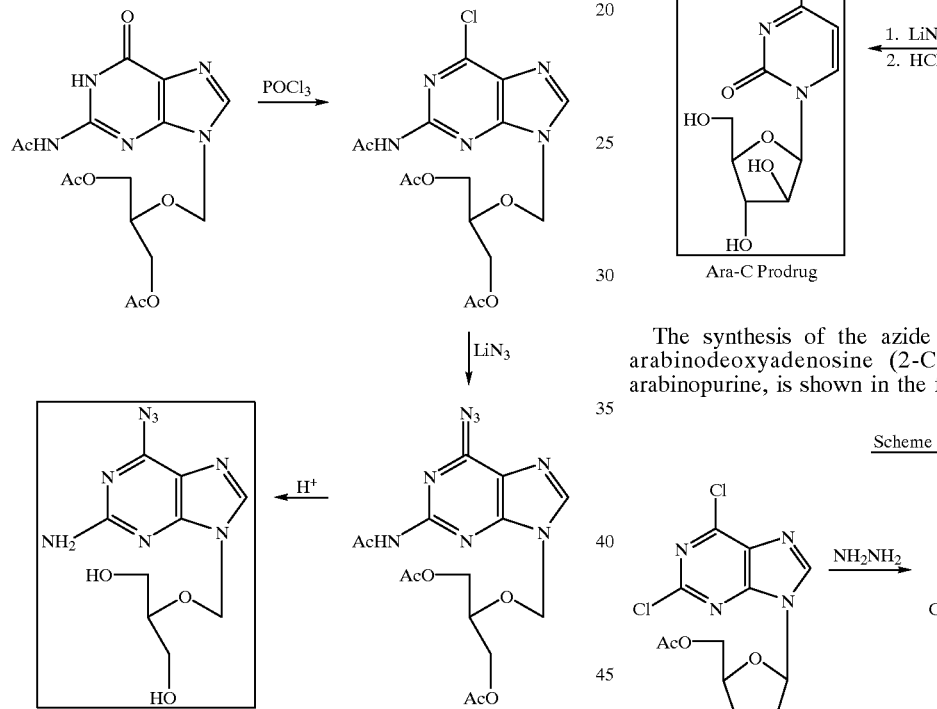

The synthesis of the azide derivative for cytarabine, 4-azido-1-β-D-arabinofuranosyl-2(1H)-pyrimidinone, is shown in the following scheme:

Scheme 9

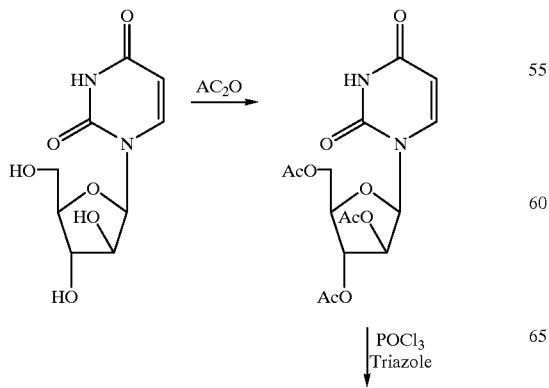

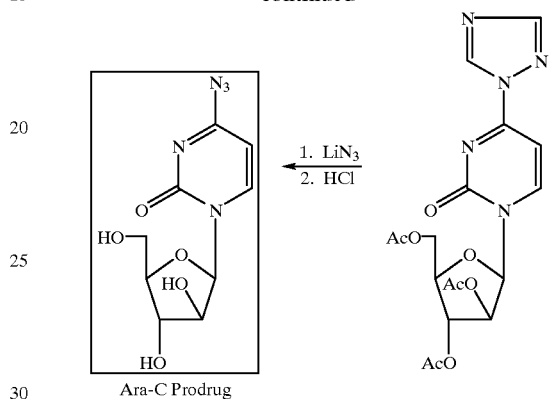

Ara-C Prodrug

The synthesis of the azide derivative for 2-chloro-9-arabinodeoxyadenosine (2-CdA), 2-chloro-6-azido-5-arabinopurine, is shown in the following scheme:

Scheme 10

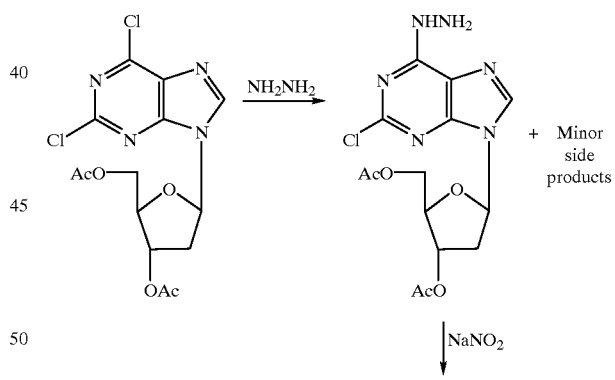

Aliphatic compounds may be prepared by treating with trifluoromethylsulfonyl azide according to the following scheme:

Scheme 11

$$RNH_2 \xrightarrow{RSO_2N_3} R-N_3$$

Care must be taken in the synthesis of aliphatic azide derivatives due to the explosive nature of trifluoromethyl-sulfoyl azide. As will be appreciated by those skilled in the art, care must also be taken to preserve the stereochemistry of the drug being converted to the corresponding azide.

EXAMPLES

Example 1
Synthesis of Cordycepin Derivative.

The cordycepin derivative, $N^6$-azido-β-D-3'-deoxyribofuranosyl purine, was synthesized according to the following scheme:

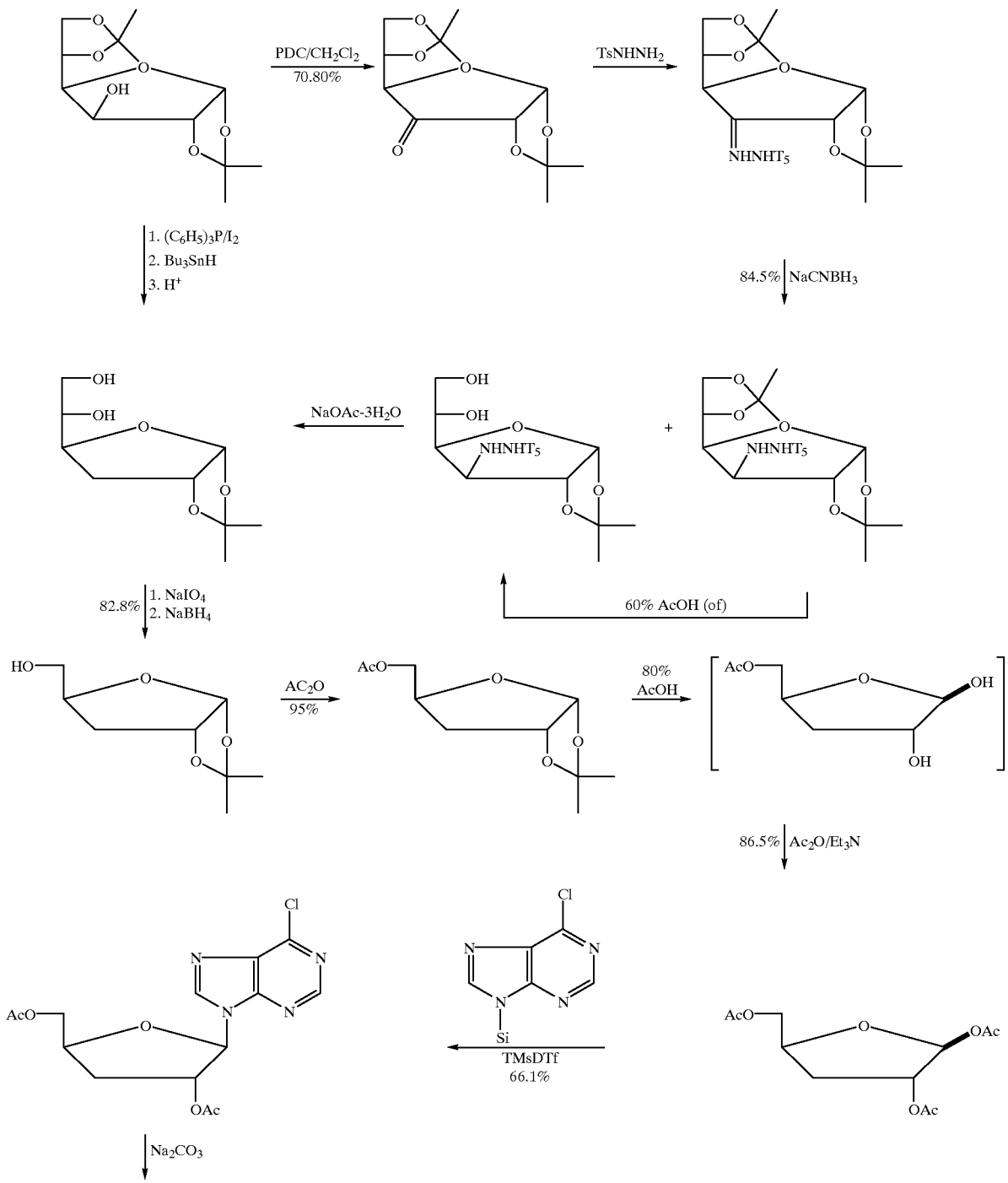

Scheme 12

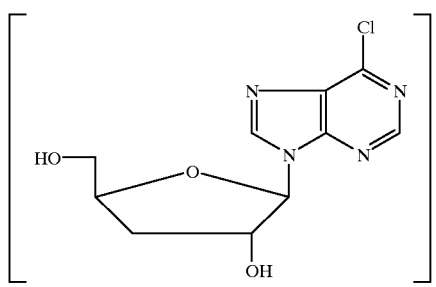

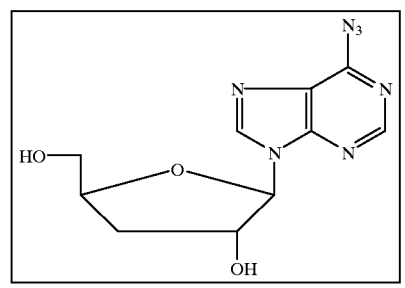

Cordycepin Prodrug

Diaceton-D-glucose (156 g 0.6 mol.) was stirred in 1000 ml CHCl$_2$. To this solution were added pyridimium dichromate (PDC 135 g 0.36 mol) and Ac$_2$O (186 ml 1.98 mol). The mixture was refluxed for 30 min. After concentration, the residue was diluted with EtOAc (500 ml), filtered and the filtrate was filtered through a silica gel pad and was washed with EtoAc. The combined filtrate was concentrated and was evaporated with toluene to give an oil, 110 g, yield: 70.8%.

A solution of this oil (110 g 0.42 mol) and TSNHNH$_2$ (86.1 g, 0.46 mol) in absolute EtOH (600 ml) was refluxed for 3 hours. After cooling, the white crystalline product was filtered and washed with MeOH (60 g., yield: 39%).

To a stirred solution of this white crystalline substance (60 g, 0.23 mol) in THP-MeOH (1:1, 700 ml) was added a trace of methyl orange and NaCNBH$_3$ (15.1 g, 10.24 mol). Methanolic HCl was added dropwise keeping the color of the solution at the red-yellow transition point. The mixture was stirred at room temperature for one hour. A second portion of NaCNBH$_3$ (8.7 g, 0.14 mol) was added, followed by dropwise addition of methanolic HCl to maintain pH 3. After stirring at room temperature for one hour, the mixture was neutralized with NaHCO$_3$ and was concentrated to dryness. The residue was dissolved in H$_2$O (150 ml) and was extracted with CH$_2$Cl$_2$ (200 ml×3), the organic layer was washed with brine and dried, filtered and evaporated to give a yellowish oil which was purified by silica gel column to give compound A as an oil (30 g) and compound B as a white solid (30 g). Compound A was dissolved in 60% HOAc (450 ml) and was stirred at room temperature overnight. The mixture was neutralized with NaHCO$_3$ (solid) and was extracted with CH$_2$Cl$_2$ (200 ml×3). The organic layer was washed with brine, dried, and filtered and evaporated to give a yellowish oil which was purified by silica gel column to give another 16 g compound B. Total yield: 84.5%.

A mixture of Compound B (46 g, 0.118 mol) and NaOAc.3H$_2$O (64.6 g, 0.48 mol) in absolute EtOH (600 ml) was refluxed for one hour. The mixture was concentrated to dryness, the residue was dissolved in H$_2$O (150 ml) and was extracted with EtOAc (200 ml×5). The organic layer was combined and was washed with brine (200 ml×2), dried and filtered, then evaporated to give a yellowish oil which was purified by silica gel column to give a yellowish oil. 20 g, yield: 83%.

To a solution of this yellowish oil (20 g, 0.099 mol) in MeOH (300 ml), NaIO$_4$ (24.6 g, 0.115 mol) in H$_2$O (200 ml) was added at 0° C. After the mixture was stirred for 10 minutes, NaBH$_4$ (5.7 g, 0.149 mol) was added and the mixture was stirred for another ten minutes. After filtration, the filtrate was concentrated to dryness and the residue was purified by silica gel column to give a white solid. 14 g, yield: 82.8%.

A mixture of this white solid (3.45 g, 20 mmol), DMAP (50 mg) Ac$_2$O (2.26 ml, 24 mmol) and Et$_3$N (4.18 ml. 30 mmol) in CH$_2$Cl$_2$ (50 ml) was refluxed for one hour. After cooling, the mixture was washed with water and brine, the organic layer was dried, filtered and evaporated to dryness to obtain a yellowish oil. 4.1 g, yield: 95%.

A mixture of this yellowish oil (13.5 g, 62.9 mmol) in 50 ml 80% HOAc was stirred at 70° C. for 24 hours. The mixture was refluxed for another hour. The mixture was concentrated to dryness and was coevaporated with toluene. The brown residue was dissolved in CH$_2$Cl$_2$ (200 ml) and Ac$_2$O (6.5 ml, 69.2 mmol), Et$_3$N (11.4 ml, 81.8 mmol), DM)0.AP (100 mg) were added. The mixture was refluxed for one hour. Due to the incompletion of the reaction, another 2 ml Ac$_2$O, 4 ml Et$_3$N were added, and the mixture was refluxed for another three hours. After cooling, the mixture was washed with H$_2$O (50 ml×2), dried, filtered and concentrated to dryness. The residue was purified by silica gel column to give a light yellow oil.

A mixture of 6-chloropurine (0.45 g, 2.9 mmol), HMDS (12 ml) and ammonium sulfate (50 mg) was refluxed for one hour. The resulting clear solution was concentrated in vacuo under anhydrous conditions. The residue was dissolved in dry Ch$_2$Cl$_2$ (75 ml) and was cooled to 0° C. To this cooled solution, the light yellow oil (0.5 g, 1.9 mmol) in CH$_2$Cl$_2$ (10 ml) and TMSOH (fresh opened, 0.6 ml, 3 mmol) were added. The temperature was then brought up to room temperature and the mixture was stifrred for 30 minutes. The mixture was stirred at room temperature for another hour. Saturated NaHCO$_3$ was added to quench the reaction. After separation, the aqueous layer was extracted with EtOAc (50 ml×2). The combined organic layer was dried, filtered and evaporated to dryness. The residue was then purified by silica gel column to obtain a colorless oil. 450 mg, yield: 66.1%.

To a solution of this colorless oil (3.69 g, 10.4 mmol) in MeOH (300 ml) was added saturated Na2CO$_3$ (3 ml to pH=8). The mixture was stirred at room temperature for 30 minutes. The mixture was neutralized with HOAc to pH 6 to 7. The mixture was concentrated to dryness and was coevaporated with toluene to give a white solid. To this solid, DMF (700 ml) and NaN$_3$ (1.1 g, 17 mmol) were added and the mixture was stirred at 60° C. for three hours. After concentration, the residue was melted with HOAc (100 ml). The white solid was filtered out, the filtrate was concentrated to dryness. After adding MeOH (50 ml), a white solid was precipitated. After filtration, a white crystal was obtained. 1.4 g, yield: 48.6%.

Example 2
Bioactivity of Cordycepin Derivative.

Female NIH Swiss mice (Harland Sprague-Dawley, Indianapolis, Ind.) weighing 24–28 g were used for pharmacokinetic experiments. 100 mg/kg of cordycepin or the azide derivative of cordycepin were administered intravenously (iv) (dissolved in methylsulfoxide (20 mg/ml)), or orally (dissolved in 30% glycerin (8.3 mg/ml)). Three animals for each time point were sacrificed at 0.08, 0.25, 0.5, 0.75, 1.0, 1.5, 2.0, 3.0 and 4.0 h after drug administration. Blood (serum) was collected and immediately analyzed.

Concentrations of the inosine derivative, cordycepin and the azide derivative of cordycepin in serum were measured by high-performance liquid chromatography (HPLC).

To measure cordycepin and its metabolite concentrations in serum, 200 pl serum sample, 50 µl of internal standard 2'-F-ddI (5 µg/ml) and 50 µl 2 M perchloric acid as a protein precipitant were added to polypropylene microcentrifuge tubes (1.5 ml). An AzdU was used as an internal standard (20 µg/ml) to measure the azide derivative concentrations in serum. Tubes were vortexed and centrifuged at 9,000 rpm for 5 min.

To neutralize, perchloric acid supernatant was transferred into a clean tube with 160 µl of concentrated sodium tetraborate solution (pH 6.5). Tubes were vortexed again and centrifuged at 12,000 rpm for 15 min. Samples were held at 0° C. during analysis.

Chromatographic separations were carried out on a Shimadzy gradient HPLC system (Shimadzy Corporation, Kyoto, Japan), which was equipped with a Model SPD-10A UV detector, a Model L-10AS pump, a Model SIL-10A autosampler, a controller Model SCL-10A and a Model CR-501 reporting integrator. Chromatography was performed on an Alltech Hypersil ODS (5 µm particle size, 4.6×250 mm, Ailtech Associates, Deerfield, Ill.) to determine cordycepin and its metabolite. The azide derivative of cordycepin was analyzed on an Alltech Hypersil BDS column (5 µm particle size, 4.6×250 mm, Alltech Associates, Deerfield, Ill.).

The mobile phase for cordycepin and metabolite analysis in serum consisted of 3% acetonitrile in 20 mM sodium borate and 10 mM EDTA (pH 6.5) at a flow of 1.4 ml/min and the mobile phase for azide derivative analysis in serum consisted of 3% acetonitrile 20 mM in potassium phosphate (pH 4.0) at a flow of 1.5 ml/min. The UV detector was set at 258 nm for analysis of cordycepin and metabolite and at 290 nm for the azide derivative.

Standard curves were prepared for each type of sample by adding known amounts of compounds to serum and subjecting them to the extraction procedure as described above. The limit of quantitation was 0.05 µg/ml for cordycepin and metabolite and 0.5 µg/ml for the azide derivative.

Plasma concentration versus time data for nucleosides were analyzed by noncompartment methods. The area under concentration versus time curves (AUC) from time zero to the last measured concentration was determined by the linear trapezoidal rule and the AUC from the time of the last measured concentration to infinity was determined by dividing the last determined concentration by the least squares elimination rate constant ($\lambda_z$). Half-life was calculated from $0.693/\lambda_z$. The variance of estimated AUC values was calculated as described by Rocci, M. L. Jr. and Jusko, W. J., "LAGRAN program for area and moments in pharmacokinetic analysis," Comp. Prog. Biomed. (1983) 16:203–216.

Absolute bioavailability (F) of the azide derivative was calculated from $AUC_{or}/AUC_{iv}$, where AUC values were determined from serum nucleoside concentration versus time data.

Relative exposures for cordycepin and its metabolite in serum after or versus iv administration of the derivative were calculated from $AUC_{or}/AUC_{iv}$.

TABLE 1

Pharmacokinetic parameters of azide derivative, cordycepin and metabolite in mouse serum after intravenous and oral administration of azide derivative at a dose of 100 mg/kg

| Compound | $AUC_{0 \to \infty}$ (mg h/L) | | F | $r_e$ | $T_{½}$ (hr) | |
|---|---|---|---|---|---|---|
| | iv | oral | | | iv | oral |
| Azide Deriv. | 47.2 ± 4.01 | 44.5 ± 2.78* | 0.94 | — | 0.36 | 0.53 |
| Cordycepin | 2.17 ± 0.35 | 1.63 ± 0.15* | — | 0.75 | 0.24 | 0.76 |
| Metabolite | 3.68 ± 0.26 | 5.89 ± 0.59** | — | 1.60 | 0.5 | 0.65 |

$r_e$ - relative exposure: AUC ratio oral vs. intravenous ($AUC_{or}/AUC_{iv}$)
*- statistically insignificant difference
**- statistically significant difference After iv administration of 100 mg/kg cordycepin, the nucleoside was rapidly eliminated from mouse blood such that there was only a trace amount of cordycepin in serum samples collected at 5 min. In serum samples collected 10 min later, cordycepin was not recovered. Neither 3'-deoxyinosine nor cordycepin were detected in serum after oral administration of 100 mg/kg cordycepin.

Figure 1B:
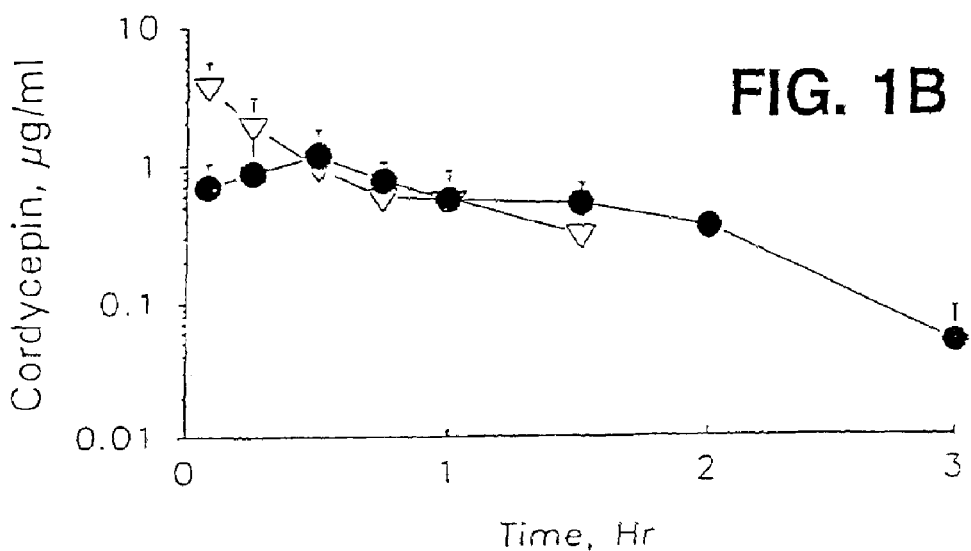
FIG. 1B shows the profile for cordycepin.
Figure 1C:
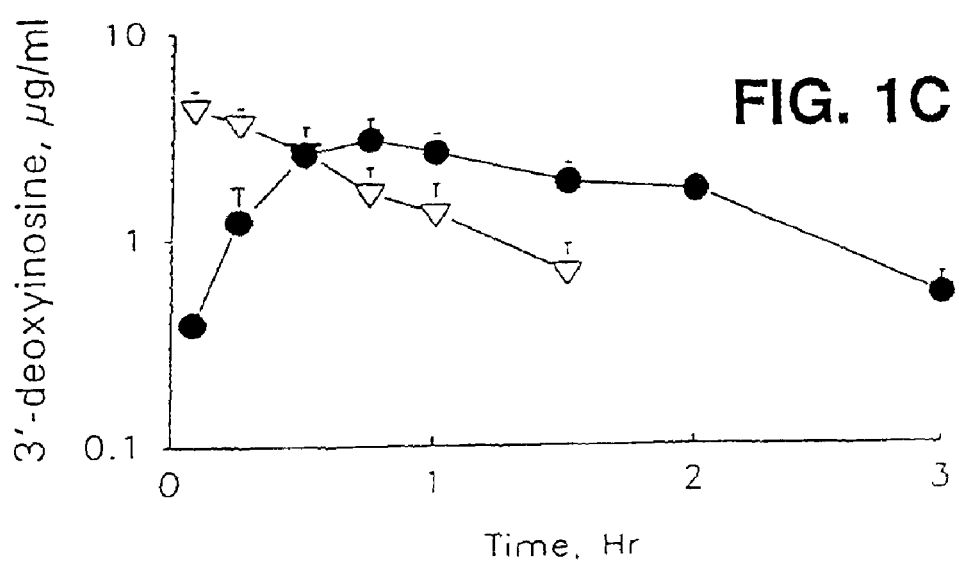
FIG. 1C shows the profile for the 3'-deoxyinosine metabolite.

The most important finding of this study was made after administration of the azide derivative to mice. Following iv and oral administration, a measurable amount of cordycepin was detected. The pharmacokinetic profiles of cordycepin as well as the azide derivative and the 3'-deoxyinosine metabolite are illustrated in FIG. 1. Pharmacokinetic parameters for the compounds are listed in Table 1.

The maximal measured concentrations ($C_{max}$) of the azide derivative were 143±33.4 µg/ml at 5 min after iv and 48.2±12.3 µg/ml at 15 min. after oral administration. The half-life values were 0.35 h (iv) and 0.53 h (oral). Absolute bioavailability (F) of the azide derivative was 0.94, but the difference between the AUC values for iv and oral administration is statistically insignificant (Table 1).

The $C_{max}$ values of cordycepin were 3.89±1.72 µg/ml at 5 min. after iv and 1.18±0.60 µg/ml at 30 minutes after oral administration. The half-life values were 0.24 h (iv) and 0.76 h (oral). The formulation with the azide derivative of cordycepin allowed detection of cordycepin in serum above 0.05 µg/ml within 1.5 h (iv) and 3 h (oral). Although $r_e$ for cordycepin was 0.75, there is no statistically significant difference between the AUC values for iv and oral administration (Table 1).

The AUC level of 3'-deoxyinosine was determined after administration of the azide derivative of cordycepin. The $r_e$ was 1.6. The half-life of metabolite had the same range of value as the azide derivative and cordycepin.

These pharmacokinetic studies of the azide derivative of cordycepin show that circulation of cordycepin in mouse serum is significantly increased. The absolute bioavailability of the azide derivative after oral administration is 94% and amount of cordycepin released from the azide derivative is the same after iv and oral administration. Oral administration of the azide derivative of cordycepin results in a cordycepin concentration above the detection limit (0.05 µg/ml) for a longer period of time.

Example 3

Synthesis of 6-azido-2',3'-dideoxy-2'-fluoro-β-D-arabinofuranosylpurine (FAAddP) and N⁶-methyl-2',3'-dideoxy-2'-fluoro-β-D-arabinofuranosyladenine (FMAddA), 2'-F-ara-ddI azide prodrugs Referring to Scheme 13, the prodrugs FAAddP (4) and FMAddA (5) were synthesized from the 6-chloropurine derivative 2. Compound 2 was synthesized from 5-O-benzoyl-3-deoxy-1,2-O-isopropylidine-α-D-ribofuranose (1) according to published procedures [Shanmuganathan, K. et al., "Enhanced brain delivery of an anti-HIV nucleoside 2'-F-ara-ddI by xanthine oxidase mediated biotransformation," J. Med. Chem. (1994) 37:821–827]. Compound 2 was debenzoylated using DIBAL-H in CH₂Cl₂ at −78° C. to obtain compound 3. Upon treatment of compound 3 with LiN₃ in DMF at room temperature, the 6-azido derivative 4 was obtained in 73% yield. The treatment of compound 2 with methylamine in DMF at 80° C. for 5 hours followed by the deprotection with saturated NH₃/MeOH for 15 hours gave compound 5 quantitatively [Chu, C. K. et al., "Synthesis and structure-activity relationships of 6-substituted 2',3'-dideoxypurine nucleosides as potential anti-human immunodeficiency virus," J. Med. Chem (1990) 33:1553–1561].

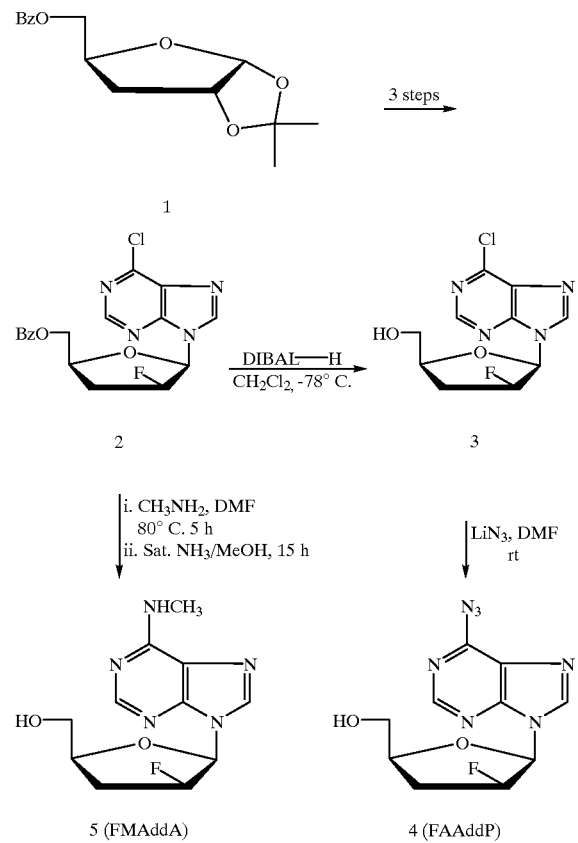

Scheme 13

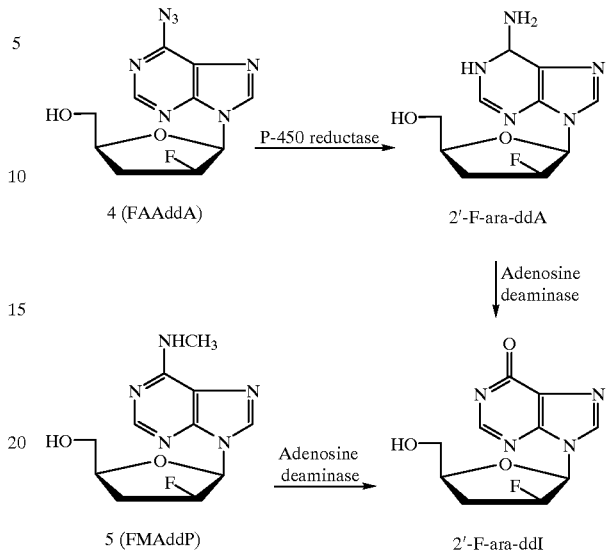

Scheme 14

Melting points were determined on a Mel-Temp II laboratory device and are uncorrected. The $^1$H NMR spectra were recorded on a JEOL FX 90 Q FT spectrophotometer, with tetramethylsilane as the internal standard; chemical shifts are reported in parts per million (δ), and the signals are quoted as s (singlet), d (doublet), t (triplet) m (multiplet), dm (double of multiplet) or brt (broad triplet). UV spectra were recorded on a Beckman DU-7 spectrophotometer. TLC were performed on Uniplates (silica gel) purchased from Analtech Co. Elemental analyses were performed by Atlantic Microlab, Inc., Norcross, Ga.

6Chloro-9-(5-O-benzoyl-2,3-dideoxy-2-fluoro-β-D-arabinofuranosyl)purine (2): Compound 2 was prepared from compound 1 according to previously published procedures [Shanmuganathan, K. et al., "Enhanced brain delivery of an anti-HIV nucleoside 2'-F-ara-ddI by xanthine oxidase mediated biotransformation, J. Med. Chem. (1994) 37:821–827]. UV (MeOH) $\lambda_{max}$ 263.5 nm (reported in Shanmuganathan, K. et al., "Enhanced brain delivery of an anti-HIV nucleoside 2'-F-ara-ddI by xanthine oxidase mediated biotransformation, J. Med. Chem. (1994) 37:821–827, as UV (MeOH) $\lambda_{max}$ 263.5 nm).

6-Chloro-9-(2,3-dideoxy-2-fluoro-β-D-arabinofuranosyl)purine (3): A solution of compound 2 (1.34 g, 3.56 mmol) in CH₂Cl₂ (40 mL) was cooled to −78° C. under nitrogen and DIBAL-H (10.5 mL, 1M solution in CH₂Cl₂) was added slowly. The reaction mixture was stirred at −78° C. for 45 min and quenched by the slow addition of MeOH. The reaction mixture was warmed to room temperature and the solvent was evaporated in vacuo. The residue was dissolved in hot MeOH and filtered through a pad of Celite. Upon concentration of the filtrate, the residue was purified on a silica gel column (5% MeOH in CHCl₃) to obtain pure compound 3 (0.74 g, 75%): mp 157–158° C.; UV (MeOH) $\lambda_{max}$ 263.5 nm (reported in Barchi, J. J. Jr. et al., "Potential anti-AIDS drugs. Lipophilic, adenosine deaminase-activated prodrugs," J. Med. Chem. (1991) 34:1647–1655, as UV (MeOH) $\lambda_{max}$ 260 nm); $[\alpha]_D^{25}$ +52.3 (c 0.5, MeOH) (reported in Barchi et al., supra, as $[\alpha]_D^{25}$ +55.7 (c 1.4, MeOH)).

6-Azido-9-(2,3-dideoxy-2-fluoro-β-D-arabinofuranosylopurine (4): A solution of 3 (1.0 g, 3.67 mmol) in DMF (25 mL) and LiN$_3$ (0.90 g, 18.3 mmol) was stirred at room temperature for 24 hours. The DMF was evaporated under high vacuum to yield a white solid which was boiled in MeOH and filtered 3 times to yield pure 4 (0.75 g, 73.5%) as a white solid: mp 209° C. (dec); UV (H$_2$O) λ$_{max}$ 287.5 nm (ε 7471, pH 7), 287.5 nm (ε 7327, pH 2), 234 nm (ε 9478, pH 11); $^1$H NMR (DMSO-d$_6$) δ 2.03–2.95 (m, 2H), 3.67 (brt, 1H), 5.09 (t, 1H, D$_2$O exchangeable), 5.57 (m, 1H), 6.61 (dd, 1H), 8.84 (d, 1H), 10.15 (s, 1H); Anal. (C$_{10}$H$_{10}$FN$_7$O$_2$): C, H, N.

N$^6$-Methyl-9-(2,3-dideoxy-2-fluoro-β-D-arabinofuranosyl)adenine(5) [See,Barchi, J. J. Jr. et al., "Potential anti-AIDS drugs. Lipophilic, adenosine deaminase-activated prodrugs," J. Med. Chem. (1991) 34:1647–1655; and Chu, C. K. et al., "Synthesis and structure-activity relationships of 6-substituted 2',3'-dideoxypurine nucleosides as potential anti-human immunodeficiency virus," J. Med. Chem. (1990) 33:1553–1561]: A solution of 2 (1.60 g., 4.25 mmol) in DMF (50 mL) and methylamine (3 mL) was sealed in a steel bomb and heated at 80° C. for 5 hours. After cooling, the solvent was evaporated and NH$_3$ in MeOH (150 mL) was added and stirred overnight. The evaporation of the solvent yielded crude product which was purified by silica gel column chromatography to yield pure 5 [See Barchi, J. J. Jr. et al. and Chu, C. K. et al, supra] (1.13 g, quantitative yield) as a hygroscopic foam: UV (MeOH) λ$_{max}$ 264 nm (reported in Barchi et al. and Chu et al. as UV (MeOH) λ$_{max}$ 265 nm); [α]$_D^{25}$+56.1 (c 0.58, MeOH) (reported in Barchi et al., supra, as [α]$_D^{25}$+56.57 (c 1.9, MeOH)).

In vitro stability in serum, brain and liver homogenate. Liver and brain homogenate were prepared in a 1:1 (g:mL) ratio with isotonic 0.05 M phosphate buffer, pH 7.4. FAAddP (70 μM) or FMAddA (50 μM) were added to the mouse serum, the brain homogenate or the liver homogenate and incubated in a shaker water bath at 37° C. Aliquots of 100 μL were removed at time zero and at selected times for up to 6 hours. Concentrations of the compounds were determined by HPLC.

Azido reduction assay. The analysis of azido reducing activity was described previously [Cretton, E. M. and Sommadossi, J-P., "Reduction of 2'-azido-2',3'-dideoxynucleosides to their 3'-amino metabolite is mediated by cytochrome P-450 and NADPH-cytochrome P-450 reductase in rat liver microsomes," Drug Metab. Dispos. (1993) 21:946–950].

Deamination of 2'-F-ara-ddA and FMAddA by adenosine deaminase. Samples (1.5 mL) of 2'-F-ara-ddA (80 μM) or FMAddA (50 μM) were prepared in 0.05 M isotonic phosphate buffer, pH 7.4, and placed into a shaking water bath at 37° C. The reaction was initiated by the addition of 15 μL of adenosine deaminase (type VII from calf intestinal mucosa, Sigma Chemical Co., St. Louis, Mo.). The final activity in the incubation media was 0.05 U/mL for 2'-F-ara-ddA and 1.0 U/mL for FMAddA. At specified time intervals, aliquots of 100 μL were withdrawn for the determination of 2'-F-ara-ddA and 2'-F-ara-ddI or FMAddA and 2'-F-ara-ddI concentrations.

The biotransformation of the prodrug FAAddP to 2'-F-ara-ddI probably involves a two-step metabolic process (Scheme 14). The prodrug was first metabolized to 2'-F-ara-ddA by the P-450 reductase system. A similar reduction of the azido moiety of AZT to an amino function by the cytochrome P-450 system has been recently demonstrated [Placidi, L. et al., "Reduction of 3'-azido-3'-deoxythymidine to 3'-amino-3'-deoxythymidine in human liver microsomes and its relationship to cytochrome P-450," Clin. Pharmacol. Ther. (1993) 54:168–176; Cretton, E. M. and Sommadossi, J-P., "Reduction of 2'-azido-2',3'-dideoxynucleosides to their 3'-amino metabolite is mediated by cytochrome P-450 and NADPH-cytochrome P-450 reductase in rat liver microsomes," Drug Metab. Dispos (1993) 21:946–950]. 2'-F-ara-ddA was then metabolized to 2'-F-ara-ddI by adenosine deaminase. The azido reduction assay confirmed that FAAddP was metabolized to 2'-F-ara-ddA and 2'-F-ara-ddI by the microsomal fraction of the human liver homogenate. Furthermore, in vitro biotransformation studies showed that direct conversion of FAAddP to 2'-F-ara-ddI by adenosine deaminase occurred at a negligible rate.

FAAddP was stable in phosphate buffer saline (PBS, pH 7.4) at 37° C. indicating that the compound is not susceptible to chemical hydrolysis. The in vitro biotransformation of this prodrug in mouse serum, however, was relatively rapid with a degradation half-life of 2.41 hours. Although FAAddP was metabolized in serum, no metabolites were identified. In the liver homogenate, FAAddP concentrations declined in a biphasic fashion. Over the initial 45 minutes, the prodrug was rapidly metabolized with a t$_{1/2}$ of 0.48 hours. Subsequently, the rate of conversion was much slower (t$_{1/2}$ =7.74 h) than the initial rate probably due to the depletion of cofactors. The formation of 2'-F-ara-ddI paralleled the decline of the prodrug with most of the prodrug being converted to 2'-F-ara-ddI. Only low concentrations of 2'-F-ara-ddA were detected in the liver homogenate. The biotransformation of FAAddP in brain homogenate was somewhat slower than that in the liver with a half-life of 6.1 hours. However, only 10% of the prodrug was converted to 2'-F-ara-ddI and 5% to 2'-F-ara-ddA over a 6 hour time period. Thus, similar to the studies in serum, an unidentified pathway was responsible for the disappearance of FAAddP in mouse brain.

The metabolic conversion of FMAddA to 2'-F-ara-ddI appeared to be a one-step process, facilitated by adenosine deaminase. The prodrug was stable in PBS, mouse serum and mouse brain homogenate and was slowly metabolized to 2'-F-ara-ddI in the liver homogenate (t$_{1/2}$ =9.1 h). However, upon addition of adenosine deaminase to PBS (t$_{1/2}$=0.46 h) and brain homogenate (t$_{1/2}$ =3.7 h), virtually all of the prodrug was converted to 2'-F-ara-ddI.

Animal studies. The pharmacokinetics of the active nucleoside, 2'-F-ara-ddI were investigated in mice. Animal studies were approved by the University of Georgia Animal Care and Use Committee and conducted in accordance with guidelines established by the Animal Welfare Act and the National Institutes of *Health Guide for the Care and Use of Laboratory Animals*. Female NIH-Swiss mice (Harland Sprague-Dawley, Indianapolis, Ind.) weighing 24–28 g were housed in 12 h light/12 h dark constant-temperature (22° C.) environment and had free access to standard laboratory chow and water. Animals were acclimatized to this environment for one week prior to the experiments.

2'-F-ara-ddI, dissolved in physiological saline (15 mg/mL), was administered intravenously via tail vein injection at a dose of 20 mg/kg (79 μmoles/kg). FAAddP (55 mg/kg; 197 μmoles/kg) was administered intravenously as a solution in DMSO (15 mg/mL) or orally by a gavage as a suspension in physiological saline. FMAddA, dissolved in saline (15 mg/mL), was administered intravenously at a dose 112 mg/kg (437 μmoles/kg). At selected time intervals, mice (three animals per each time point) were anesthetized with diethyl ether and sacrificed by exsanguination via left ventricular heart puncture. Serum was harvested from blood collected. The brain was excised, rinsed with normal saline, blotted dry and weighed. Serum and brain samples were frozen at −20° C. until analysis.

Analytical Methodology. Concentrations of FAAddP, FMAddA, 2'-F-ara-ddA and 2'-F-ara-ddI in PBS, serum, brain and liver homogenate were determined by high performance liquid chromatography (HPLC). The brain or liver tissue were homogenized in a 1:1 (g:mL) ratio with ice cold isotonic 0.05 M phosphate buffer, pH 7.4. Buffer, serum or tissue homogenate (100 μL) was mixed with 10 μL of internal standard (25 μg/mL of 3'-azido-2',3'-dideoxyuridine, AZddU). Acetonitrile (600 μL) containing 0.1% acetic acid was added while vortexing to precipitate proteins. The tubes were centrifuged at 3,000 rpm for five minutes and the supernatant was transferred to a clean tube. Supernatant was evaporated to dryness under a stream of nitrogen gas at room temperature. The residual film was reconstituted in 110 μL of mobile phase and 50 μL was injected onto the HPLC.

Chromatographic separations were performed using a Hypersil ODS column 150×4.5 mm, 5 μm particle size (Alltech Associates, Deerfield, Ill.) preceded by a guard column packed with 30–40 μm pellicular Perisorb RP-18. Mobile phase flow rate was 2 mL/min. For the analysis of FAAddP and 2'-F-ara-ddA, the mobile phase consisted of 7% (v/v) acetonitrile in 80 mM sodium acetate, pH 5.0. The retention times for 2'-F-ara-ddI, FAAddP and AZddU were 4.5, 7.9 and 5.1 min, respectively. The mobile phase for the analysis of 2'-F-ara-ddI consisted of 4.2% (v/v) acetonitrile in 40 mM sodium acetate, pH 4.1, yielding retention times of 3.78 and 7.6 min, for 2'-F-ara-ddI and AZddU, respectively. For the analysis of FMAddA in serum and liver homogenate, a mobile phase of 7.5% acetonitrile in 40 mM sodium acetate, pH 6.0 was used. The retention time for FMAddA was 8.8 min and that for AZddU was 4.9 min. For FMAddA analysis in brain homogenate, the mobile phase consisted of 7.5% acetonitrile in 10 mM $K_2HPO_2$ (pH 7.2) yielding retention times for FMAddA and AZddU of 7.8 and 4.3 min, respectively. Eluants were monitored at a UV wavelength of 260 nm.

Nucleoside standards ranging from 0.04 μg/mL to 100 μg/mL, prepared in blank PBS, serum, brain homogenate and liver homogenate were treated the same as unknown samples. Samples with nucleoside concentrations greater than 100 μg/mL were diluted with the appropriate blank matrix. The limit of quantitation (signal-to-noise ratio of 3:1) for the 2'-fluoronucleosides in all biological media was 0.1 μg/mL. Extraction recovery was greater than 80% for all compounds. The intra- and inter assay relative standard deviations (RSDs) for each compound were less than 10% in all media.

Data analysis in vitro studies. Linear regression of the natural logarithm of nucleoside analogue concentrations as a function of time were used to determine first-order degradation rate constants (k) and associated half-lives ($t_{1/2}$ =0.693/k) in PBS, serum, liver homogenate and brain homogenate.

Data analysis in vivo studies. Nucleoside concentration as a function of time data were analyzed by a non-compartmental technique. The AUC under the serum or brain nucleoside mean (n=3) concentration versus time curve and the first moment (AUMC) were determined by Lagrange polynomial interpolation and integration from time zero to the last sample time ($AUC_{0-\tau}$) with extrapolation to time infinity using the least-squares terminal slope ($\lambda_z$) (Rocci, M. L. Jr. and Jusko, W. J., "LAGRAN program for ara and moments in pharmacokinetic analysis," Comp. Prog. Biomed. (1983) 16:203–216]. The last 3 to 5 time points were used to obtain $\lambda_z$. Half-life was calculated from $0.693/\lambda_z$. For intravenously administered compounds, total clearance ($CL_T$) was calculated from Dose/AUC and steady-state volume of distribution ($V_{SS}$) from Dose×AUMC/$AUC^2$. The fraction of the prodrug converted to parent compound ($f_c$) was calculated from $AUC_{\leftarrow pd} \times CL_T / Dose_{pd}$. where $AUC_{p \leftarrow pd}$ is the AUC of the parent compound after administration of the prodrug ($Dose_{pd}$) and $CL_T$ is the clearance of the parent compound [Gibaldi, M. and Perrier, D., "Clearance concepts." In: *Pharmacokinetics,* 2nd ed., Marcel Dekker Inc., New York (1982) 319–353]. Relative brain exposure ($r_e$) was calculated from $AUC_{brain}/AUC_{serum}$.

Figure 2:
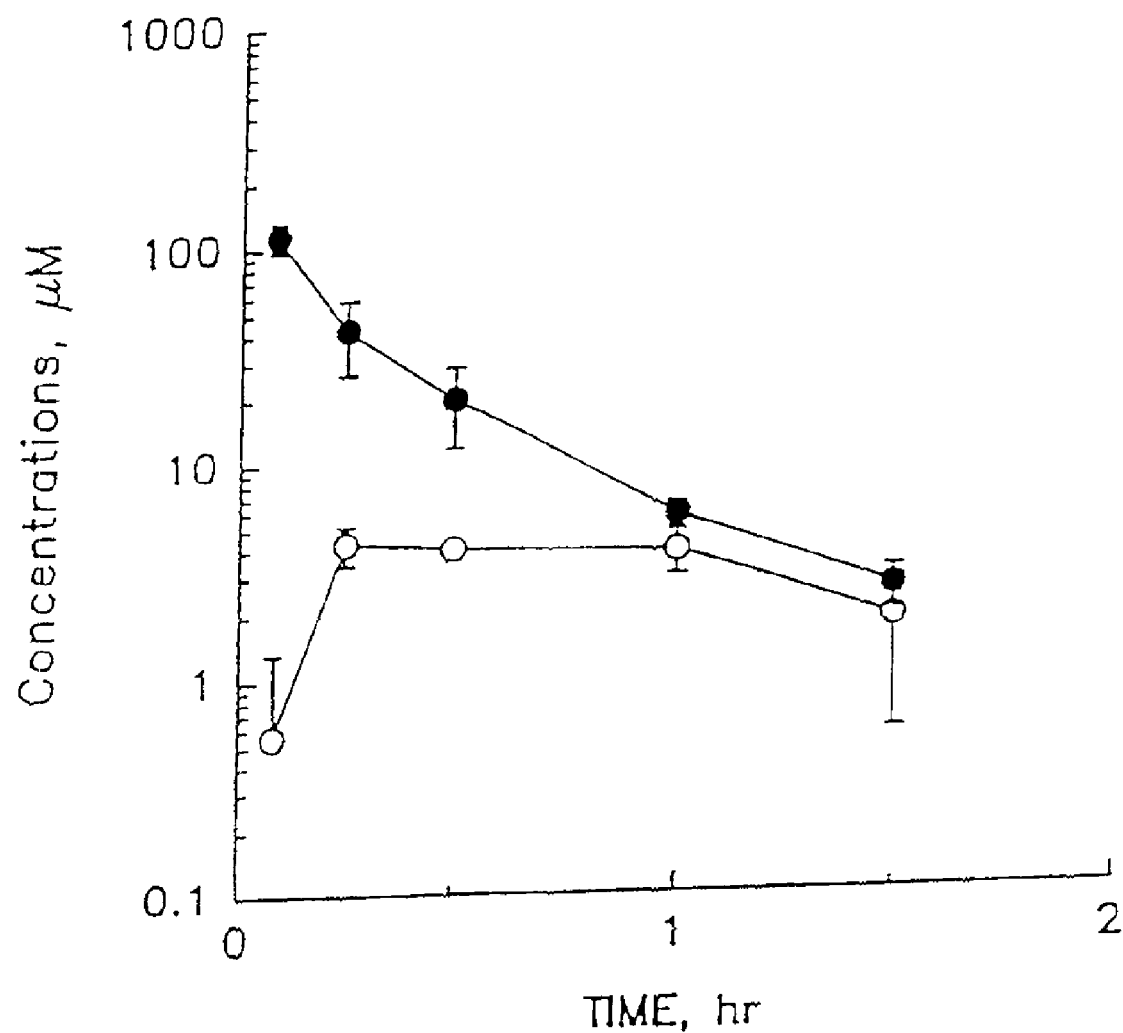
FIG. 2 shows mean±SD serum (●) and brain (○) concentrations of 2'-F-ara-ddI after intravenous administration of 20 mg/kg 2'-F-ara-ddI to mice.

Concentrations of 2'-F-ara-ddI in serum and brain after intravenous administration of 20 mg/kg of the compound are illustrated in FIG. 2. Serum concentrations of 2'-F-ara-ddI declined rapidly with a half-life of 0.41 h (Table 2). Brain concentrations of the nucleoside peaked at approximately 20 minutes, remained relatively constant for 30 minutes, and subsequently declined in parallel with serum concentrations. Relative brain exposure ($r_e$) of the 2'-fluoronucleoside was 16.5%. Total clearance of 2'-F-ara-ddI was 2.18 L/h/kg and was moderate relative to the hepatic blood flow (5 L/h/kg) and renal blood flow (3.6 L/h/kg) in mice [Gerlowski, L. E. and Jain, R. K., "Physiologically based pharmacokinetic modeling: principles and applications," J. Pharm. Sci. (1983) 72:1103–1126]. Steady-state volume of distribution was 0.78 L/kg hence, indicating that the compound was distributed intracellularly to a moderate extent.

TABLE 2

Pharmacokinetics parameters for 2'-F-ara-ddI, FAAddP, 2'-F-ara-ddA and FMAddA following administration of 20 mg/kg of 2'-F-ara-ddI or 55 mg/kg of FAAddP or 112 mg/kg of FMAddA to mice.

| Compound administered Compound measured | Dose (mg/kg) | Route of Administration | Substrate | $AUC_{0-\tau}$ (μM · h) | AUG (μM · h) | $t_{1/2}$ (h) | AUC/Dose (μM · h/μmol/kg) |
|---|---|---|---|---|---|---|---|
| 2'-F-ara-ddI | | | | | | | |
| 2'-F-ara-ddI | 20 | iv | Serum | 36.2 | 38.0 | 0.41 | 0.48 |
| | | | Brain | 5.6 | 6.3 | 0.47 | 0.08 |
| FAAddP | | | | | | | |
| FAAddP | 55 | iv | Serum | 199.3 | 199.8 | 0.22 | 1.01 |
| | | | Brain | 12.0 | 12.6 | 0.22 | 0.06 |
| 2'-F-ara-ddA | | | Serum | 3.0 | 8.6 | 2.92 | 0.04 |
| | | | Brain | 3.9 | 4.8 | 0.91 | 0.02 |
| 2'-F-ara-ddI | | | Serum | 26.5 | 26.9 | 0.68 | 0.13 |
| | | | Brain | 4.8 | 5.3 | 0.96 | 0.03 |

TABLE 2-continued

Pharmacokinetics parameters for 2'-F-ara-ddI, FAAddP, 2'-F-ara-ddA and FMAddA following administration of 20 mg/kg of 2'-F-ara-ddI or 55 mg/kg of FAAddP or 112 mg/kg of FMAddA to mice.

| Compound administered<br>Compound measured | Dose<br>(mg/kg) | Route of<br>Administration | Substrate | $AUC_{0-\tau}$<br>($\mu M \cdot h$) | AUG<br>($\mu M \cdot h$) | $t_{1/2}$<br>(h) | AUC/Dose<br>($\mu M \cdot h/\mu mol/kg$) |
|---|---|---|---|---|---|---|---|
| FAAddP | | | | | | | |
| FAAddP | 55 | oral | Serum | 34.2 | 37.5 | 1.53 | 0.19 |
| | | | Brain | ND* | ND | ND | ND |
| 2'-F-ara-ddA | | | Serum | 0.8 | 1.0 | 1.74 | 0.005 |
| | | | Brain | ND | ND | ND | ND |
| 2'-F-ara-ddI | | | Serum | 6.7 | 9.2 | 2.92 | 0.046 |
| | | | Brain | ND | ND | ND | ND |
| FMAdda | | | | | | | |
| FMAdda | 112 | iv | Serum | 296.8 | 298.8 | 0.46 | 0.68 |
| | | | Brain | 39.0 | 39.5 | 0.98 | 0.09 |
| 2'-F-ara-ddI | | | Serum | 10.1 | 11.2 | 0.52 | 0.025 |
| | | | Brain | ND | ND | ND | ND |

*ND - Not Detected.

Figure 3A:
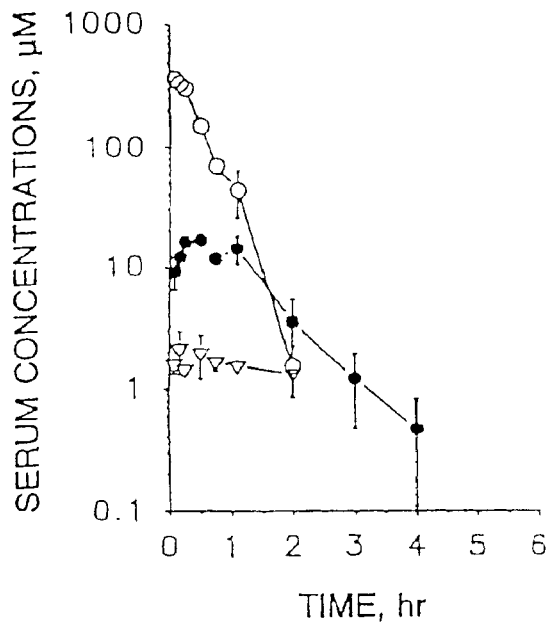
FIG. 3 shows mean±SD concentrations of FAAddP (○), 2'-F-ara-ddA (∇) and 2'-F-ara-ddI (●) in serum (A) and brain (B) after intravenous administration and in serum (C) after oral administration of 55 mg/kg FAAddP to mice.
Figure 3B:
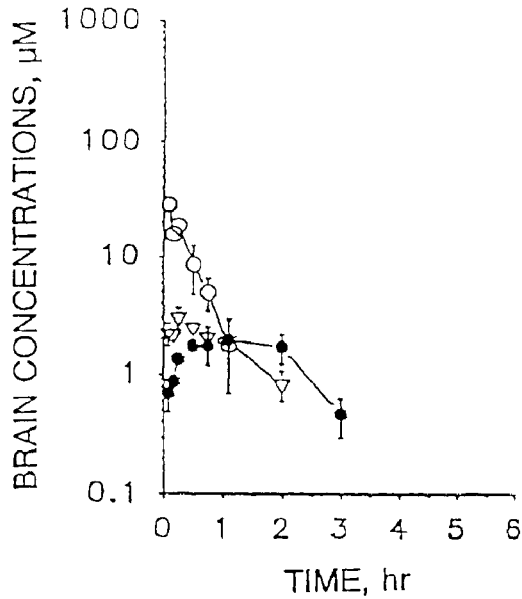

Concentrations of FAAddP, 2'-F-ara-ddA and 2'-F-ara-ddI in the serum and the brain after intravenous administration of 55 mg/kg of FAAddP are shown in FIG. 3 (A and B). Serum concentrations of the prodrug declined rapidly with a half-life of 0.22 h (Table 2). Total clearance and steady-state volume of distribution of the prodrug were 1.12 L/h/kg and 0.58 L/kg, respectively. Thus, clearance of FAAddP was two-fold slower than that of 2'-F-ara-ddI and the distribution was slightly less extensive. In serum samples, low levels of 2'-F-ara-ddA and higher concentrations of 2'-F-ara-ddI were observed. The elimination half-life of 2'-F-ara-ddI after FAAddP administration was longer than that after the administration of 2'-F-ddI. The elimination half-life of 2'-F-ara-ddA was 2.9 h. The higher concentration of 2'-F-ara-ddI compared to 2'-F-ara-ddA is in agreement with the results of the in vitro studies. Approximately 30% of the intravenously administered dose of the FAAddP was converted to 2'-F-ara-ddI.

FAAddP distributed rapidly into the brain with peak brain levels observed at the first sampling time (FIG. 2B). The relative brain exposure of the prodrug was 6.3%, while that of 2'-F-ara-ddA and 2'-F-ara-ddI were 55.8% and 19.7%, respectively. Thus, brain exposure to FAAddP was relatively low and the relative brain exposure to 2'-F-ara-ddI after intravenous administration of FAAddP was similar to that after administration of 2'-F-ara-ddI. Although the relative brain exposure for 2'-F-ara-ddA was relatively high, brain concentrations were low.

To compare the disposition of 2'-F-ara-ddI after the administration of FAAddP to that after the administration of 2'-F-ara-ddI, AUC (area under curve) values were normalized for dose. As shown in Table 2, the dose normalized AUC values for 2'-F-ara-ddI in the serum and the brain after intravenous administration of 55 mg/kg of FAAddP were 3- to 4-fold lower than after the administration of 20 mg/kg of 2'-F-ara-ddI.

Figure 3C:
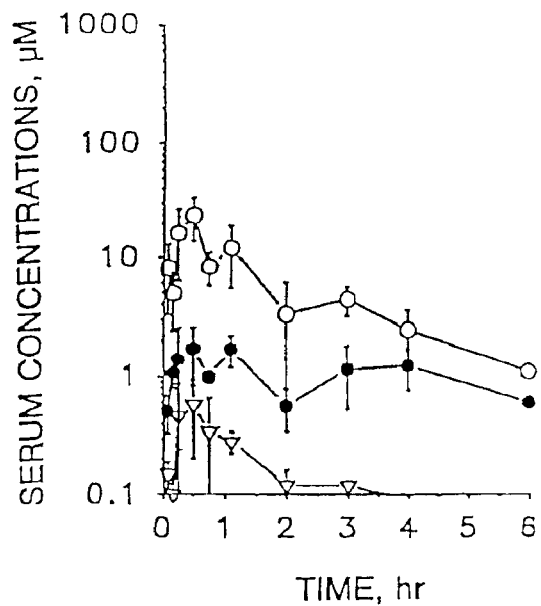

Concentrations of FAAddP, 2'-F-ara-ddA and 2'-F-ara-ddI in the serum after oral administration of 55 mg/kg FAAddP are depicted in FIG. 3C. Absorption of FAAddP was rapid with peak serum concentrations of the compounds achieved 0.5 hours after dosing. Oral bioavailability of FAAddP was 19%, indicating incomplete absorption owing in part to its poor solubility. Brain concentrations of FAAddP, 2'-F-ara-ddA and 2'-F-ara-ddI were below the limit of quantitation because of the low oral bioavailability of FAAddP. Similar to intravenous study of FAAddP, higher concentrations of 2'-F-ara-ddI when compared to 2'-F-ara-ddA were observed, suggesting that the metabolism of FAAddP to 2'-F-ara-ddA is the rate limiting step in the formation of 2'-F-ara-ddI.

Figure 4A:
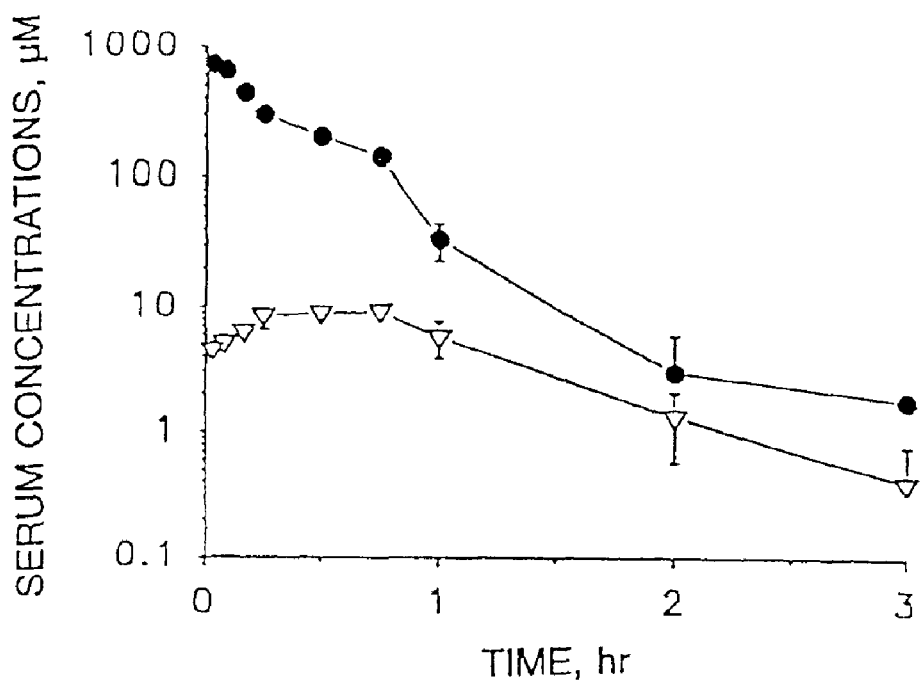
FIG. 4 shows mean±SD serum (A) and brain (B) concentrations of FMAdda (●) and 2'-F-ara-ddI (∇) after intravenous administration of 55 mg/kg FMAddA to mice.
Figure 4B:
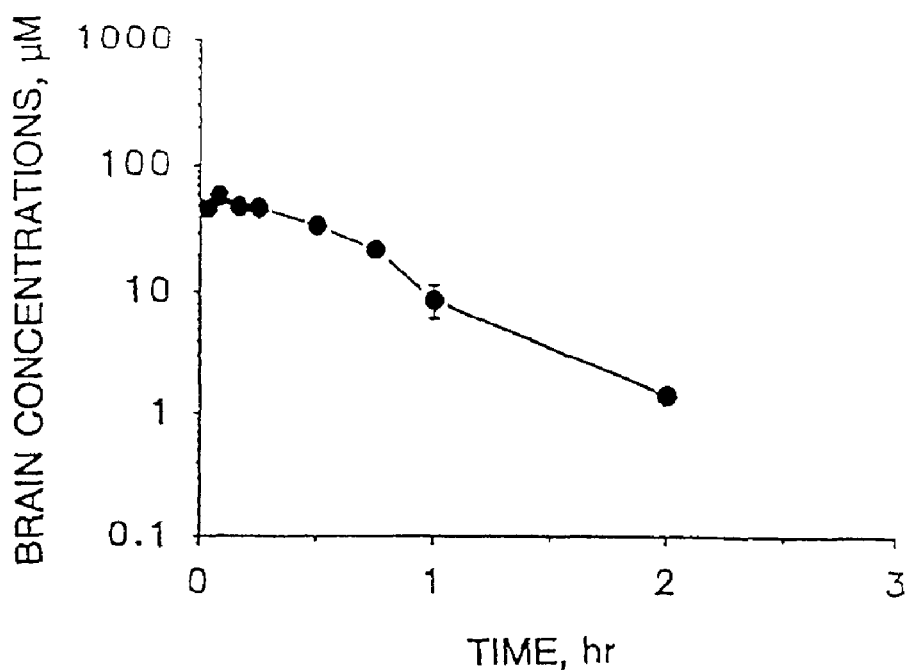

As with FAAddP, a higher dose of FMAddA had to be administered to measure the levels of 2'-F-ara-ddI. Concentrations of FMAddA and 2'-F-ara-ddI in serum and brain after intravenous administration of 112 mg/kg of FMAddA are depicted in FIG. 4. Serum concentrations of FMAddA declined rapidly with a half-life of 0.45 h (Table 2). Total clearance (1.93 L/h/kg) and steady-state volume of distribution of FMAddA (0.79 L/kg) were similar to those of 2'-F-ara-dedI. Only 5.6% of the administered prodrug was converted to 2'-F-ara-ddI due to the low levels of ADA in mice. The relative brain exposure of the prodrug was 7.5%; however, inconsistent with in vitro studies, no 2'-F-ara-ddI was detected in brain samples even at the relatively high dose administered.

In summary, FAAddP underwent reduction to 2'-F-ara-ddA followed by deamination to the active compound 2'-F-ara-ddI. FMAddA did not result in increased brain delivery of the prodrug and was too slowly converted to 2'-F-ara-ddI to prove to be effective. In this study, a new approach was demonstrated in the design of azido prodrugs by utilizing the P-450 NADPh reductase system.

Example 5

Synthesis of 9-β-D-arabinofuranosyl-6-azidopurine (6-AAP) the azide derivative of AraA.

The azide derivative for Ara-A was synthesized according to the following scheme 15:

Scheme 15

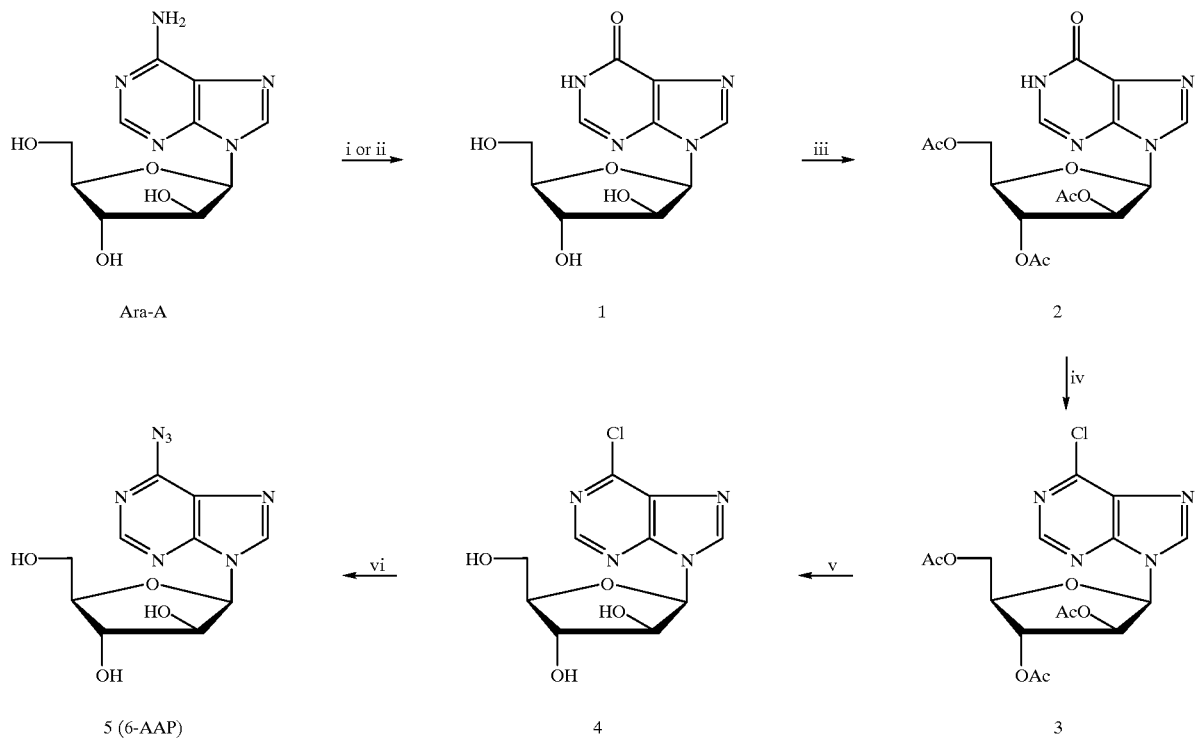

(i) NaNO₂, AcOH, 36 h; (ii) Adenosine deaminase, Water, 16 h; (iii) Ac₂O, Pyridine, 0° C., 16 h; (iv) SO₂Cl₂, Ch₂Cl₂, DMF, reflux, 2 h; (v) NH₃, MeOH, 2 h; (vi) Lithium azide, DMF, 2 days.

The target compound 5 (6-AAP) was synthesized from ara-A (scheme 15). Ara-A was deaminated to 9-(β-D-arabinofuranosyl)hypoxanthine (1) using adenosine deaminase in >90% yield. This method was found superior in comparison to the deamination procedure with NaNO₂/AcOH. Compound I was peracetylated with acetic anhydride in pyridine, then converted to its 6-chloro derivative 3 under refluxing conditions with thionyl chloride (26% from 1) [Robins, M. J. and Bason, G. L., "6-Chloro-9-(2-deoxy-β-D-erythro-pentofuranosyl)purine from the chlorination of 2'-deoxyinosine," In: Nucleic Acid Chemistry; Townsend, L. B., Tipson, R. S., Eds.; John-Wiley & Sons: New York (1978) Part II, pp. 601–606]. Compound 3 was deprotected to compound 4 by treatment with ammonia in methanol and subsequently treated with LiN₃ in DMF to obtain compound 5 (6-AAP) (38% from 3).

The stability of 6-AAP at pH 2, 7 and 11 and towards adenosine deaminase hydrolysis was studied by UV spectroscopy. At pH 2 and 7, 6-AAP did not show any significant change over a period of 2.75 hours at 287.5 nm (37° C.). However, at pH 11, 6-AAP immediately changed its UV absorption maximum from 287.5 nm to 222.5 nm. 6-AAP was not hydrolysed by adenosine deaminase for up to three hours in a separate in vitro study performed in phosphate buffer (pH 7.4) at 25° C. These results show that unlike ara-A, 6-AAP is not a substrate for ADA.

Materials: Melting points were determined on a Mel-Temp II laboratory device and are uncorrected. The ¹H NMR spectra were recorded on a JEOL FX 90 Q FT spectrophotometer, with TMS as the internal standard; chemical shifts are reported in parts per million (δ), and the signals are quoted as s (singlet), d (doublet), t (triplet) or m (multiplet). UV spectra are recorded on a Beckman DU-650 spectrophotometer. TLC was performed on Uniplates (silica gel) purchased from Analtech Co. Elemental analysis was performed by Atlantic Microlab, Inc., Norcross, Ga. Ara-A and Adenosine deaminase (Type II crude powder from calf intestinal mucosa, 1–5 units/mg activity) was purchased from Sigma chemical Co., St. Louis, Mo. All other chemicals are of reagent grade. Methanol and acetonitrile, methyl sulfoxide were purchased from EM Science, Gibbstown, N.J.

9-β-D-Arabinofuranosyl hypoxanthine (1): Method A. To a solution of ara-A (500 mg, 1.87 mmol) in glacial acetic acid (8 ml), NaNO₂ (258 mg, 3.73 mmol) dissolved in 1 ml of water, was added and stirred for six hours. Then another three portions of NaNO₂ (200 mg, 2.8 mmol) each for every six hours were added and stirring continued. After 36 hours, the solvent was evaporated in vacuo and the residue was recrystallized from hot water (25 ml) to obtain pure 1 (339 mg, 67.6%). UV(MeOH)λ$_{max}$ 249.0 nm, 207.0 nm.

Method B: To a suspension of ara-A (500 g, 1.87 mmol) in distilled water (30 ml) was added adenosine deaminase (4 mg), and the mixture was stirred for 16 hours. Then the water was evaporated under reduced pressure and the white residue obtained was recrystallized from hot water (20 ml) to obtain compound 1 as soft white solid (462 mg, 92%). UV (MeOH) λ$_{max}$ 248.5 nm, 205.5 nm.

9-(2,3,5-Tri-O-acetylarabinofuranosyl)hypoxanthine (2): To a suspension of 1 (335 mg, 1.25 mmol) in dry pyridine (5 ml), acetic anhydride (1 ml 10.5 mmol) was added at 0° C. and the mixture was stirred for 16 hours. Then the solvent was evaporated in vacuo, the residue was dissolved in 50 ml of methylene chloride and was washed with water (2×50 ml), sat. NaHCO₃ solution, brine and was dried (anhyd. sodium sulfate). The organic layer was concentrated in vacuo to obtain a brownish yellow solid 3 (339 mg, crude yield 68%) which was used in the subsequent reaction without any further purification. UV(MeOH) $\lambda_{max}$ 250.0 nm, 206.0 nm.

6Chloro-9-(2,3,5-tri-Oacetyl-β-D-arabinofuranosyl)purine (3). Crude compound 2 (130 mg) was dissolved in dry $CH_2Cl_2$ (10 mL) and heated to 55° C. Dry DMF (1 mL) followed by a 2 M solution of $SOCl_2$ in $CH_3Cl_2$ (2.43 mL, 0.57 mmol) were added dropwise over a period of 45 minutes. The reaction mixture was gently refluxed for an additional 75 minutes. The reaction mixture was cooled to room temperature and diluted with $CH_2Cl_2$. The organic layer was washed with saturated $NaHCO_3$ solution (2×50 mL), brine (50 mL) and dried (anhydrous sodium sulfate). The organic phase was concentrated in vacuo and purified by preparative TLC (5% $MeOH/CHCl_3$) to obtain pure 3 (50 mg, 26% from 1): UV (MeOH)$\lambda_{max}$ 263.0 nm, 212.5 nm.

9-(β-D-Arabinofuranosyl)-chloropurine (4). Compound3 (200 mg,0.5 mmol) was dissolved in saturated $NH_3$/MeOH (5 mL) and stirred at room temperature for two hours. The solvent was evaporated in vacuo to obtain crude 4 (170 mg) which was used for the subsequent reaction without any further purification: UV (MeOH)$\lambda_{max}$ 263.0 nm.

9-(β-D-Arabinofuranosyl)-6azidopurine (5). A solution of 4 (170 mg, 0.63 mmol) in DMF (5 ml) was treated with lithium azide (270 mg, 5.52 mmol) and stirred for two days at room temperature. The solvent was evaporated under reduced pressure at 40° C. and the crude oil was recrystallizd from MeOH to obtain pure 5 (67 mg, 38.4%): mp 185–190° C. (dec.); UV$\lambda_{max}$ (water) pH 2: 205.0 (15,506), 287.0 (6,496); pH 7: 208.5 nm (12,943), 287.5 nm (6033); pH 11: 222.5 nm (6,730); $^1H$ NMR (DMSO-$d_6$) δ 3.66–3.90 (m, 3H, H-5', H-4'), 4.16–4.33 (m, 2H, H-2', H-3'), 5.14 (t, 1H, 5'-OH, exchangeable with $D_2O$), 6.50 (d, 1H, H-1'), 8.75 (s, 1H, H-8), 10.12 (s, 1H, H-2); IR (KBr) 2037, 1649; Anal. ($C_{10}H_{11}N_7O_4$.0.65 $CH_3OH$): C, H, N.

Stability studies of 6AAP. A kinetic study at varying pHs (pH 2, 7 and 11 at 37.1° C.) was performed on a UV spectrophotometer to investigate the stability of 6-AAP. At pH 11, the UV absorption maximum for compound 5 shifted from 287.5 nm to 222.5 nm immediately. At pH 7, the compound did not show any significant change in UV absorption maxima over a period of 2.75 hours at 287.5 nm indicating that it is stable at the neutral pH. At pH 2, the compound was stable.

Comparative in vWtro studies were performed in mice liver homogenate by separately incubating 6-AAP and 6-AAP/coformycin to investigate the biotransformation of 6-AAP alone and in the presence of ADA inhibitor, coformycin (Table 3). The half-lives of 6-AAP in the absence and presence of coformycin were 4.90 hours and 5.98 hours, respectively. Ara-A was detected in both cases and the corresponding half-lives were 1.45 hours and 2.58 hours, respectively. When ara-A alone was incubated in the mouse liver homogenate, its half-life was 0.04 hours. Thus, the half-life of ara-A generated from 6-AAP alone was 36 times greater than that of ara-A itself. Azido reduction assay utilizing the microsomal fraction of human liver homoge nate also confirmed that 6-AAP was converted to ara-A as shown in mice liver homogenate studies. The biotransformation of 6-AAP to ara-A involves the cytochrome P450 NADPH dependent system (scheme 16). The stability and metabolism of 6-AAP were also studied in mice serum and brain homogenate (Table 3). The half-lives of 6-AAP in mice serum and brain homogenate were 3.73 hours and 7.29 hours, respectively. The decline of 6-AAP in serum was biphasic with a slow decline in the initial one hour period ($T_{1/2}$ =3.73 h) and then with a faster decline rate ($T_{1/2}$ =1.41 h).

TABLE 3

Parameters for the in vitro biotransformation of 6-AAP and ara-A in mice.

| Compound | Medium Analyte | $K_{el}$ ($h^{-1}$) | $T_{1/2}$ (h) |
| --- | --- | --- | --- |
| 6-AAP* | Liver homogenate | | |
| | 6-AAP | 0.14 | 4.66 |
| | Ara-A | 0.48 | 1.46 |
| | Ara-H | 0.26 | 2.45 |
| 6-AAP and coformycin | Liver homogenate | | |
| | 6-AAP | 0.12 | 5.98 |
| | Ara-A | 0.27 | 2.58 |
| Ara-A | Liver homogenate | | |
| | Ara-A | 16.87 | 0.04 |
| | Ara-H | 0.31 | 2.24 |
| 6-AAP | Serum[§] | | |
| | 6-AAP | 0.25 | 3.73 |
| 6-AAP | Brain homogenate | | |
| | 6-AAP | 0.01 | 7.29 |

*Average of two studies and the liver homogenate was prepared by addition of 1 or 1.5 weight equivalents of water.
[§]These values were calculated from 0 to 1 h after the incubation. The decline of 6-AAP concentration in serum was biphasic with a slow decline in the first 1 hour and then with a faster decline ($T_{1/2}$ = 1.4 h).

Figure 5:
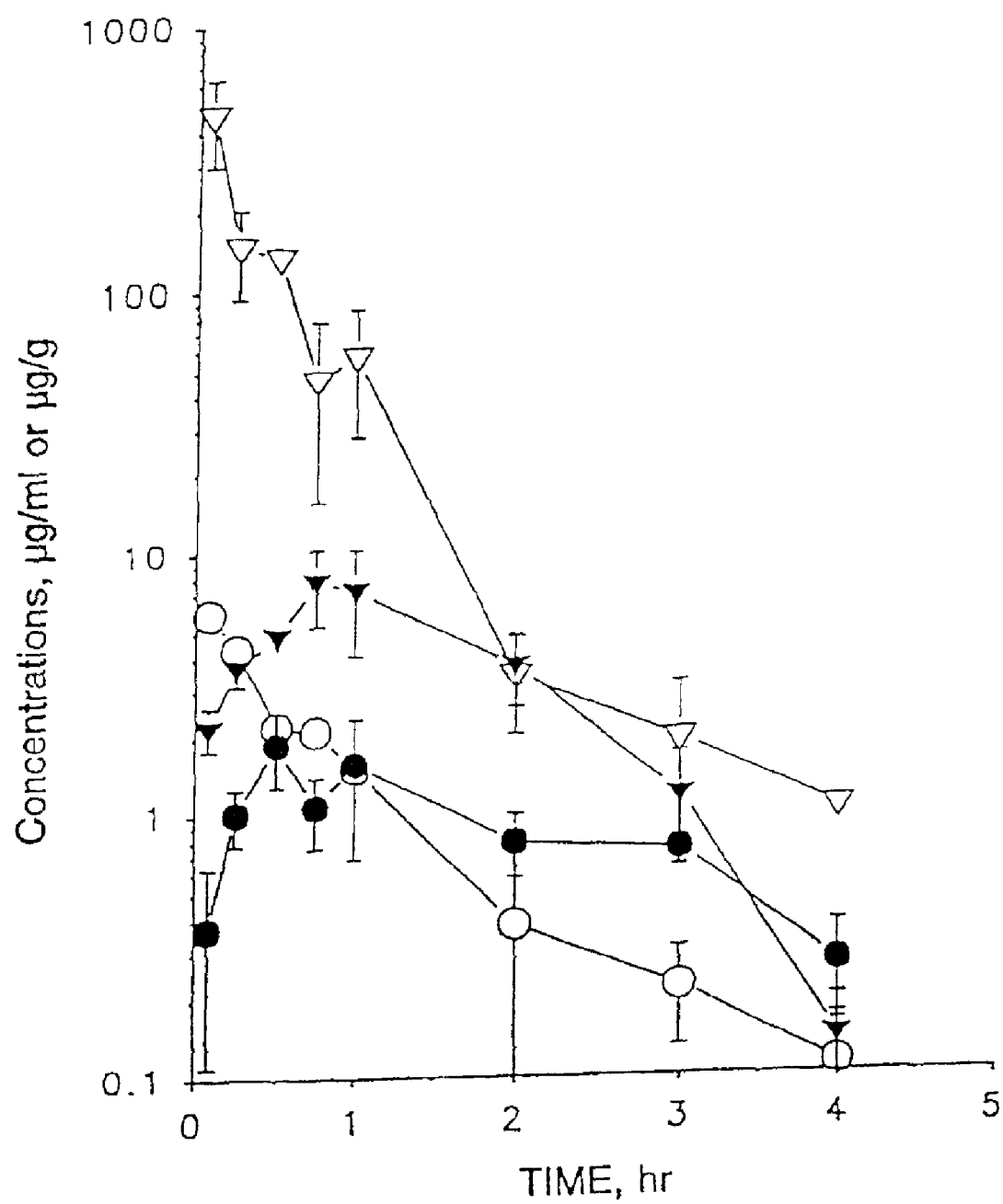
FIG. 5 shows mean±SD concentrations of 6-AAP in serum (μg/ml) after intravenous (∇) and oral (▼) administration, and in brain (μg/g) after intravenous (○) and oral (●) administration of 100 mg/kg of 6-AAP to mice.

Following these interesting in vitro results, in vivo pharmacokinetic studies were performed in mice. FIG. 5 shows the mean serum concentrations of 6-AAP versus time after intravenous and oral administration of 100 mg/kg of 6-AAP. The corresponding pharmacoldnetic parameters for 6-AAP are presented in Table 4. Maximum concentration of 6-AAP in serum was observed after five minutes of intravenous and after 60 minutes of oral dosing (FIG. 5). Maximum concentrations of 6-AAP in serum after intravenous and oral dosing were 465±167 μg/mL and 7.8±2.51 μg/mL, respectively. The terminal mean half-life values (0.55 hour and 0.58 hour for intravenous and oral, respectively) were similar for both routes of administration. The area-under-curve (AUC) values for serum concentration versus time for 6-AAP were 201.1±17.9 mg.h/L and 13.77±1.4 mg.h/L, respectively following intravenous and oral administration of 100 mg/kg of 6-AAP. After intravenous administration of 20 mg/kg of 6-AAP, the AUC value was 85.6 mg.h/L (data not not shown), a 5-fold difference in the AUC values after intravenous dosing of 20 and too mg/kg of 6-AAP, which indicates that the disposition of 6-AAP in mice followed linear kinetics in the dose interval between 20 mg/kg and 100 mg/kg.

Scheme 16

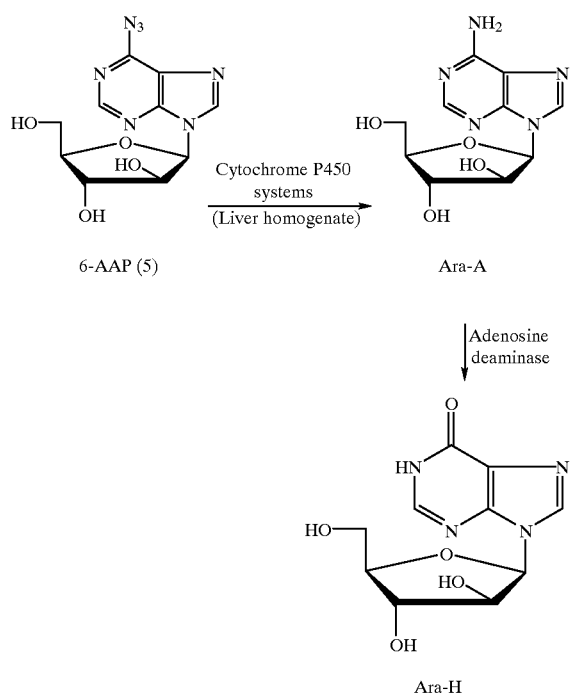

(1.29 h) than that after intravenous administration (0.77 h). The relative brain exposure ($r_e$) value of 6-AAP was also greater after oral dosing (0.3) than that after intravenous administration (0.02) of 6-AAP.

Figure 6:
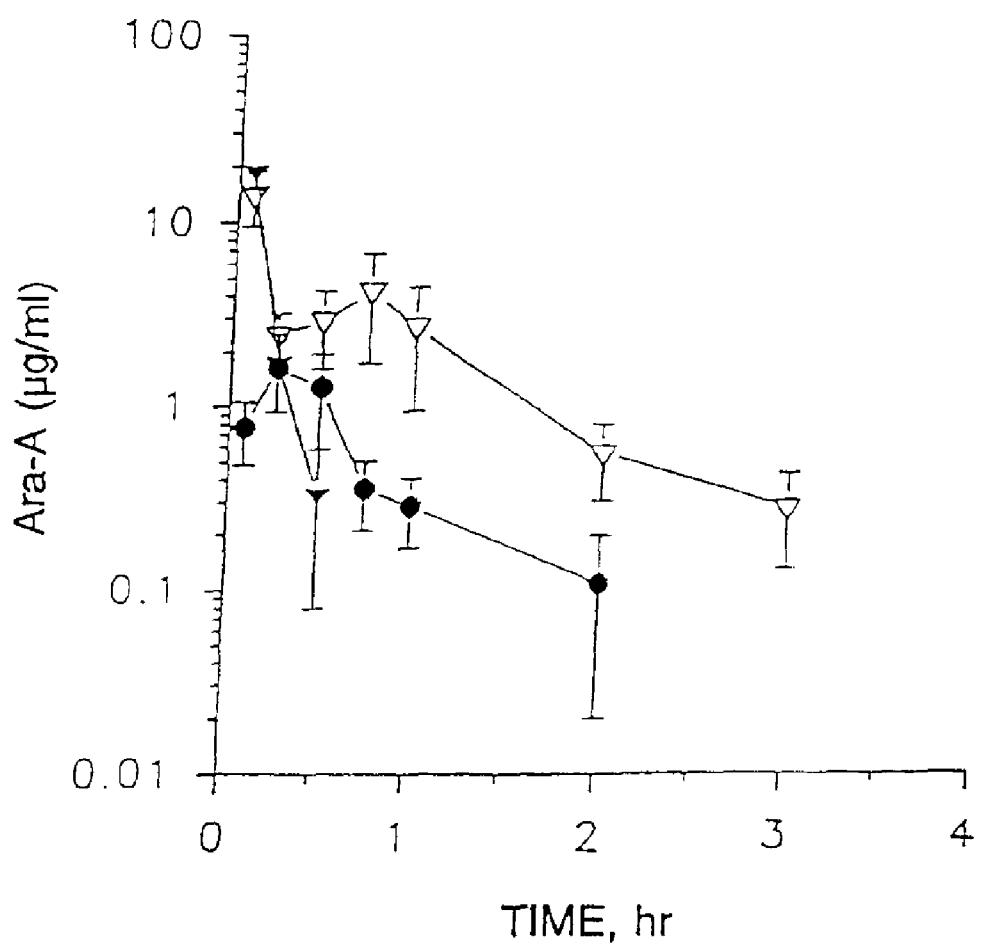
FIG. 6 shows mean±SD serum concentrations of ara-A after intravenous administration of ara-A (▼) and ara-A after oral (●) and intravenous (∇) administration of 100 mg/kg of 6-AAP to mice.

The serum concentrations of ara-A versus time after the administration of ara-A (intravenous) and 6-AAP (oral and intravenous) are shown in FIG. 6. After the intravenous administration of ara-A, a significant fraction of the compound was rapidly metabolized and its level declined from 18.5±3.5 μg/mL to 0.33±0.25 μg/mL in 25 minutes. The AUC value was 3.95±0.2 mg.h/L and the half-life was 0.07 h. However, the pharmacokinetics curves for ara-A in serum after the intravenous administration of 6-AAP were different from those after the intravenous administration of ara-A. This curve revealed a "retard decline" of ara-A in serum with a significant increase in the half-life (0.89 h). Ara-A level was 0.28±0.15 μg/mL after three hours of the injection. The AUC value (6.84±0.89 mg.h/mL) is 73% higher than that after the ara-A administration (3.95±0.20 mg.h/L) (Table 4). When 6-AAP (100 mg/kg) was administered orally, the serum AUC value of ara-A (1.15±0.13 mg.h/L) was 29% of that after the intravenous administration of ara-A (3.95±0.20 mg.h/L) and the half-life was 0.45 hours.

TABLE 4

Pharmacokinetic parameters of ara-A, 6-AAP and ara-A released from 6-AAP after dosing of 100 mg/kg of ara-A or 6-AAP.

| Compound Administered | Route of Administration | Compound Measured | Tissue | AUC (mg · h/L) | $t_{1/2}$ (h) | $r_e$ (brain) |
|---|---|---|---|---|---|---|
| ara-A | iv | ara-A | serum | 3.95 ± 0.20 | 0.07 | — |
|  |  |  | brain | ND* | — | — |
| 6-AAP | iv | 6-AAP | serum | 201.1 ± 17.9 | 0.55 | — |
|  |  |  | brain | 4.41 ± 0.37 | 0.77 | 0.02 |
|  |  | ara-A | serum | 6.84 ± 0.89 | 0.89 | — |
|  |  |  | brain | 0.35 ± 0.04 | 1.47 | 0.05 |
| 6-AAP | oral | 6-AAP | serum | 13.77 ± 1.40 | 0.58 | — |
|  |  |  | brain | 4.12 ± 0.37 | 1.29 | 0.30 |
|  |  | ara-A | serum | 1.15 ± 0.13 | 0.45 | — |
|  |  |  | brain | 1.55 ± 0.57 | 5.03 | 1.35 |

*ND - Not detected.

Figure 7:
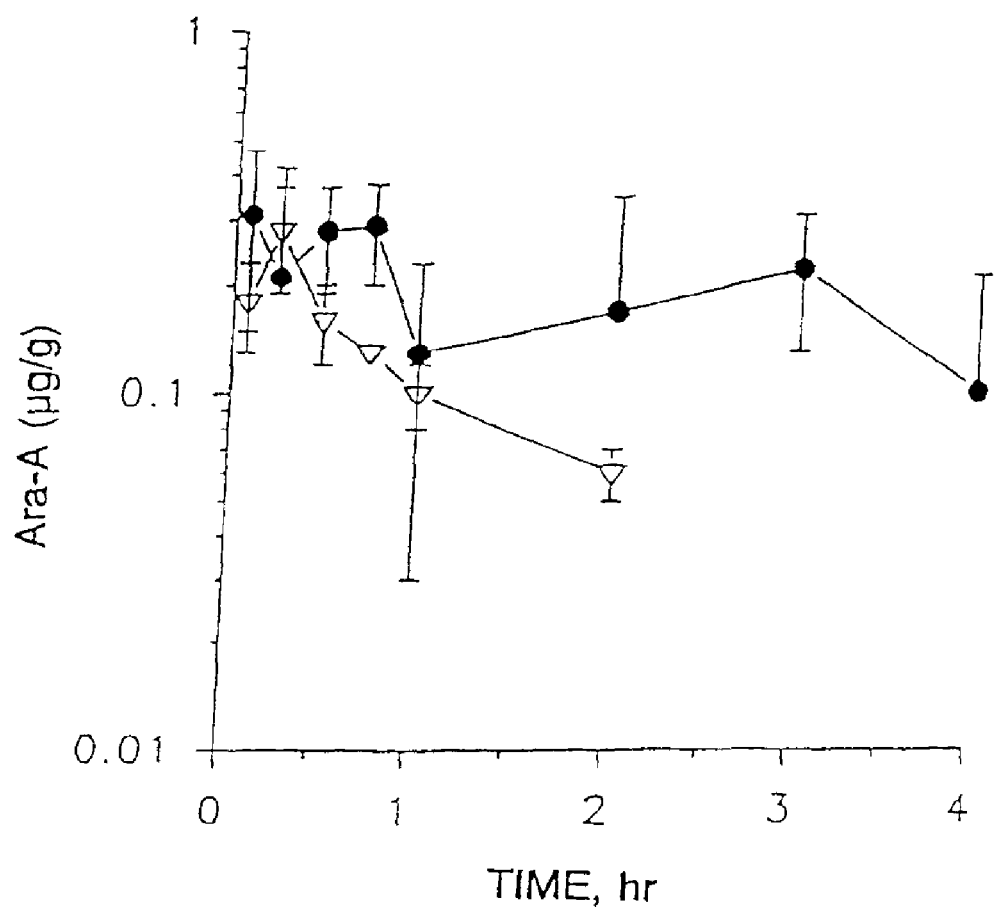
FIG. 7 shows mean±SD brain concentrations of ara-A after oral (∇) and intravenous (∇) administration of 100 mg/kg of 6-AAP to mice.

The concentrations of 6-AAP in brain versus time after its intravenous and oral administration are shown in FIG. 5. After intravenous and oral administrations of 6-AAP, the maximum concentrations of 5.92±0.7 and 1.87±μg/g in the brain were observed at 5 and 30 minutes, respectively. The brain AUC values for 6-AAP were almost the same for both (intravenous and oral) routes of administration (4.41±0.37 and 4.12±0.37 mg.h/L, respectively) (Table 4). The serum AUC levels of 6-AAP were 201±17.9 mg.h/L and 13.77±1.40 mg.h/L after intravenous and oral administration of 6-AAP. In comparison, the brain AUC levels of 6-AAP were 2% and 33% of serum AUC levels after intravenous and oral administration of 6-AAP, respectively. This data suggests that there may be a saturable transport process of 6-AAP into the brain. Half-life of 6-AAP in the brain was approximately two-fold greater after oral administration The brain concentrations of ara-A after the administration of 6-AAP versus time are illustrated in FIG. 7. Ara-A was not found in the brain after its intravenous administration in a dose of 100 mg/kg. However, ara-A converted from 6-AAP exhibited a relatively constant mean concentration in the brain of 0.3 to 0.1 ug/g from 5 minutes to 120 minutes after intravenous administration and from 5 minutes to 240 minutes after oral administration of 6-AAP. The greater distribution in the brain was characterized by the increase in the brain AUC, $r_e$ and half-life values for ara-A after oral administration (1.55±0.57 mg.h/L, 1.35 and 5.03 hours, respectively) versus intravenous administration (0.35±0.04 mg.h/L, 0.05 and 1.47 hours, respectively) of 6-AAP (Table 4).

Adenosine deaminase studies. 6-AAP (0.22 μM/mL) was incubated with adenosine deaminase (0.05 mg/mL) in phosphate buffer (pH 7.4) at 25.1° C. and the change in the concentration was observed at 278.5 nm for three hours.

Analysis. Concentrations of ara-A and 6-AAP in serum, brain (whole or homogenate) and liver homogenate were measured by high-performance liquid chromatography (HPLC). Chromatographic separations were carried out on Millipore gradient system, which was equipped with a Model 486 tunable UV detector, two Model 510 pumps, a Model 717 plus autosampler, and a Millennium 2010 Chromatography Manager software (Millipore Corporation, Milford, Mass.). All the solvents were of HPLC grade. Chromatography was performed on an Altech Hypersil ODS $C_{18}$ (5 μm particle size, 4.5×150 mm, Altech Associates, Deerfield, Ill.). The mobile phase A was 0.5% acetonitrile in 2.5 mM $KH_2PO_4$(pH 6.8), mobile phase B was 12% acetonitrile in 2.5 mM $KH_2PO_4$ (pH 6.8), mobile phase C was 2.5 mM $KH_2PO_4$ (pH 5.2) and mobile phase D was 23% methanol in 2.5 mM $KH_2PO_4$.

In vitro metabolism study. Female NIH Swiss mice (Harland Sprague-Dawley, Indianapolis, Ind.) were sacrificed and serum, liver and brain tissues were collected before each experiment. Serum was collected from several animals. The brain and liver were washed in normal saline at 4° C., wiped and then weighed. Either 1 or 1.5 weight equivalents of water were added to the tissue and homogenized using a homogenizer. The homogenate was divided into two halves: one portion was used as the blank and the other for incubation with either ara-A, 6-AAP or &AAP/coformycin in a water bath shaker at 37° C. Initial concentrations of 6-AAP and ara-A were 100 μg/mL. Samples and blanks of volume 400 μL were collected at 0, 5, 15, and 30 minutes and at 1, 2, 3, 4 and 5 hours.

To measure the analyte concentrations in serum, liver or brain homogenate, 400 μL of sample was mixed with 50 μL of internal standard (AzdU, 5 μg/mL) and 0.7 mL of acetonitrile. After centrifugation, the supernatant was decanted to another tube and treated with anhydrous $Na_2SO_4$, then vortexed for one minute and centrifuged again. The organic layer was separated and evaporated under nitrogen stream at room temperature. The residue was reconstituted in mobile phase A and filtered through MPS-I micropartition system (3KD membranes (Amicon Inc., Beverly, Mass.) by centrifugation for 50 minutes at 2000 rpm to further clean-up the samples. 100 μL of filtrate was injected for analysis.

For the HPLC analysis, during the first 10 minutes, the flow rate was changed linearly from 1.5 mL/min to 1.0 mL/min and was continued at 1.0 mL/min until the end of assay (67 minutes). In the first 20 minutes, the mobile phase consisted of 95% A and 5% B; from 20 minutes, a linear gradient was run for 55 minutes to reach 5% A and 95% B. After each analysis, the column was equilibrated for 10 minutes to initial conditions. The $\lambda_{max}$ was set at 249 nm for the first 15 minutes to observe ara-H, from 15 to 35 minutes at 261 nm to observe ara-A, from 35 to 45 minutes at 285 nm to observe 6-AAP, and subsequently changed to 261 nm to observe AzdU. The retention time for ara-H, ara-A, 6-AAP and AzdU were 14.1, 33.8, 40.9 and 49.3 minutes, respectively.

Azido reduction study: The procedure for the analysis of azido reducing activity was described previously [Cretton, E. M. and Sommadossi, J.-P., "Reduction of 3'-azido-2',3'-dideoxynucleosides to their 3'-amino metabolite is mediated by cytochrome P-450 and NADPH-cytochrome P-450 reductase in rat liver microsomes," Drug Metab. Dispos. (1993) 21:946–950]. Briefly, incubation mixtures contained either 1.5 mg of human liver fraction protein (homogenate or supernatant fractions following centrifugation) or 1.5 mg microsomal protein, 5.0 mM $MgCl_2$, 6.0 mM NADPH and 0.4 mg/mL of 6-AAP in 0.1 M phosphate buffer saline at pH 7.4 (final volume of 0.2 mL). The reaction was initiated by adding NADPH and conducted at 37° C. for 60 minutes under nitrogen. Reactions were terminated by heating at 100° C. for 30 seconds and the proteins were removed by centrifugation at 14,000 g for six minutes. Aliquots (100 μL) were then analyzed for nucleosides by HPLC. Control incubations were performed in the absence of protein.

Inhibition of azido reduction assay: Assays were performed using 1.5 mg microsomal protein as described above following either a 45 second exposure to carbon monoxide or a 5 minute pre-incubation with 1 mM metyrapone prior to the addition of NADPH.

In vivo pharmacokinetics: Female NIH Swiss mice (Harland Sprague-Dawley, Indianapolis, Ind.) weighing 24–28 g were used for the pharmacokinetic experiments. Mice were acclimatized in a 12 h light/12 h dark, constant temperature (20° C.) environment for one week before the experiments.

In a randomized study, animals were administered with either 20 or 100 mg/kg of 6-AAP or 100 mg/kg of ara-A (intravenous). 6-AAP was also dosed orally (100 mg/kg p.o.). At least three animals each were sacrificed at 0.08, 0.025, 0.5, 0.75, 1.0, 2.0, 3.0, 4.0, 5.0 and 6.0 hours after drug administration. Blood (serum) from the heart and whole-brain samples were collected. Serum samples were treated immediately and brain samples were frozen at −20° C. until analysis. To determine the nucleoside concentrations in the serum, a know amount of serum sample, 50 μL of the internal standard (AzdU, 5 μg/mL) and 1.0 mL of acetonitrile as a protein precipitant were added to polypropylene microcentrifuge tubes (1.7 mL). Tubes were mixed and centrifuged at 9,000 rpm for 10 minutes.

To measure the ara-A and 6-AAP in the whole brain, 50 μL of internal standard (AzdU, 10 μg/ml) and 300 μL of water were added to the weighed tissue samples (approximately 300 mg). After homogenization, 1.8 mL of acetonitrile was added to tissue homogenates, samples were mixed and centrifuged at 9,000 rpm for 10 minutes. The resulting supernatant from the serum or the brain was transferred to a clean tube and dried under a stream of nitrogen gas at 22° C. The residue was reconstituted in 220 μL of mobile phase D and after centrifugation at 12,000 rpm for 40 min, 100–150 μL was injected for the HPLC analysis. During the first 28 minutes, a linear gradient from 5% C and 95% D to 20% C and 80% D was run and then during the next 20 minutes, a linear gradient was run to reach 65% C and 35% D at a flow rate of 1.5 mL/min. After each assay, the column was equilibrated to initial conditions for 7 minutes. The $\lambda_{max}$ was set at 249 nm for the first 15 minutes to observe ara-H, from 15 to 30 minutes at 261 nm to observe ara-A, from 30 to 40 minutes at 285 nm to observe 6-AAP, and then changed to 261 nm to observe AzdU. The retention time for ara-H, ara-A, 6-AAP and AzdU were 13.5, 27.8, 36.7 and 43.5 minutes, respectively.

Standard curves: Standard curves were prepared for each type of sample by adding known amounts of ara-A and 6-AAP to the serum, brain or liver and subjecting them to the extraction procedure as described above. The limit of quantitation of the ara-A and 6-AAP were 0.1 μg/mL and 0.3 μg/mL, respectively. The percent recoveries of the compounds were 63% for ara-A and 55% for 6-AAP.

Data analysis: Serum and tissue concentrations versus time data for 6-AAP and ara-A were analyzed by noncompartmental methods. The area under concentration (AUC) versus time profiles from time zero to the last measured concentration were determined by the linear trapezoidal rule and the AUC from the time of the last measured concentration to infinity was determined by dividing the last determined concentration by the least-squares elimination rate constant ($\lambda_Z$). Half-life was calculated from $0.693/\lambda_Z$. The relative tissue exposure ($r_e$) of the compounds was calculated from $AUC_{Tissue}/AUC_{serum}$. A variation of AUC was calculated according to previous procedures [Yuan, I., "Estimation of variance for AUC in animal studies," J. Pharm. Sci. (1993) 82:761–763].

6-AAP kinetics in serum: Mean 6-AAP concentration versus time profiles for serum after intravenous and oral administration of 100 mg/kg of 6-AAP were measured. The pharmacokinetic parameters for 6-AAP are presented in Table 4.

Maximum concentration of 6-AAP in serum was observed after 5 min of intravenous and after 60 min of oral dosing. Maximum concentrations of 6-AAP in serum after iv and oral dosing were 465±167 µg/ml and 7.8±2.51 µg/ml respectively. The terminal mean half-life values (0.55 h and 0.58 h for iv and oral respectively) were similar for both routes of administration. The AUC's for serum concentration versus time curve for 6-AAP were 201.1±17.9 mg.h/L and 13.77±1.4 mg.h/L following intravenous and oral administration of 100 mg/kg. After intravenous administration of 20 mg/kg of 6AAP, the AUC value was 85.6 mg.h/L. Thus, we found a 5-fold difference in the AUC values after iv dosing of 20 and 100 mg/kg of 6-AAP. This indicates that the disposition of 6-AAP in mice followed linear kinetics in the dose interval between 20 mg/kg and 100 mg/kg. Absolute bioavailability of 6-AAP was 6.8% following oral administration.

While particular embodiments of the invention have been described and exemplified, it will be understood that the invention is not limited thereto, since many modifications can be made, and it is intended to include within the invention any such modifications as fall within the scope of the claims.

What is claimed is:

1. A pharmaceutical composition adapted for delivery to a subject comprising:
   a) an azide derivative of a drug, which drug comprises an amino or hydroxyl moiety, wherein in said azide derivative an azide group occurs at the site of said amino or hydroxyl moiety in place of said moiety, said azide derivative being capable of being converted to said drug in vivo by replacement of said azide group with said amino or hydroxyl moiety of said drug; and
   b) a suitable pharmaceutical carrier, wherein said drug is a biologically active therapeutic purine compound or a purine nucleoside or purine nucleotide compound and said azide group occurs on the 6-position of said purine compound or said purine nucleoside or nucleotide compound.

2. The composition according to claim 1 wherein said drug is a purine compound.

3. The composition according to claim 1 wherein said drug is a purine nucleoside or purine nucleotide compound.

4. The composition according to claim 3 wherein said drug is a purine nucleoside compound.

5. The composition according to claim 3 wherein said drug is a purine nucleotide compound.

6. The composition according to claim 1 wherein said azide derivative has the formula

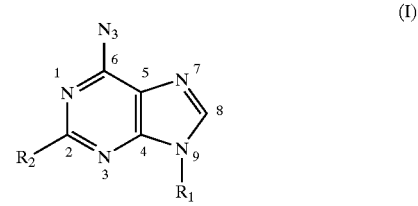

(I)

wherein $R_1$ is
(1) a substituted or unsubstituted furanose or dioxolane that is bound at the 1' position to the N9 ring nitrogen of the purine of formula (I), or is
(2) $R_3$—$OR_4$, where $R_3$ is a $C_2$–$C_5$ alkyl, alkenyl, or alkynyl and —$OR_4$ is a $C_2$–$C_5$ alkoxycarbonyl or alkoxy alcohol, and
wherein $R_2$ is H, OH, $NH_2$, or NHAc.

7. The composition according to claim 6 wherein $R_1$ is furanose, $R^3$ is a $C_2$–$C_5$ alkyl and —$OR_4$ is a $C_2$–$C_5$ alkoxy alcohol.

8. The composition according to claim 6 wherein $R_1$ is dioxolane.

* * * * *